United States Patent
Roberts et al.

(10) Patent No.: US 11,990,019 B2
(45) Date of Patent: *May 21, 2024

(54) NOTIFICATIONS ON A USER DEVICE BASED ON ACTIVITY DETECTED BY AN ACTIVITY MONITORING DEVICE

(71) Applicant: Fitbit, Inc., San Francisco, CA (US)

(72) Inventors: Timothy Roberts, San Francisco, CA (US); Nichiketa Choudhary, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,723

(22) Filed: Dec. 5, 2022

(65) Prior Publication Data

US 2023/0177941 A1 Jun. 8, 2023

Related U.S. Application Data

(63) Continuation of application No. 16/948,860, filed on Oct. 2, 2020, now Pat. No. 11,521,474, which is a
(Continued)

(51) Int. Cl.
*G08B 1/08* (2006.01)
*A61B 5/00* (2006.01)
(Continued)

(52) U.S. Cl.
CPC ........ *G08B 21/0423* (2013.01); *A61B 5/0022* (2013.01); *A61B 5/1112* (2013.01);
(Continued)

(58) Field of Classification Search
CPC ........ G08B 21/0423; G08B 3/10; G08B 5/36; G08B 6/00; G08B 21/182; A61B 5/0022;
(Continued)

(56) References Cited

U.S. PATENT DOCUMENTS

| | | | |
|---|---|---|---|
| 2,717,736 | A | 9/1955 | Schlesinger |
| 2,827,309 | A | 3/1958 | Fred |

(Continued)

FOREIGN PATENT DOCUMENTS

| | | |
|---|---|---|
| CN | 100998921 | 7/2007 |
| CN | 101380252 | 3/2009 |

(Continued)

OTHER PUBLICATIONS

"Activator is One of the Best Cydia iPhone Hacks Control you iPhone with Gestures", iphone-tips-and-advices.come, retrieved on Jul. 9, 2013 at http://www.iphone-tips-and-advice.com/activatior. htm, 10 pages.
(Continued)

*Primary Examiner* — Toan N Pham
(74) *Attorney, Agent, or Firm* — DORITY & MANNING P.A.

(57) ABSTRACT

Methods, systems and devices are provided for motion-activated display of messages on an activity monitoring device. In one embodiment, method for presenting a message on an activity monitoring device is provided, including the following method operations: downloading a plurality of messages to the device; detecting a stationary state of the device; detecting a movement of the device from the stationary state; in response to detecting the movement from the stationary state, selecting one of a plurality of messages, and displaying the selected message on the device.

20 Claims, 13 Drawing Sheets

Related U.S. Application Data continuation of application No. 16/167,240, filed on Oct. 22, 2018, now Pat. No. 10,796,549, which is a continuation of application No. 15/614,380, filed on Jun. 5, 2017, now Pat. No. 10,109,175, which is a continuation of application No. 15/202,441, filed on Jul. 5, 2016, now Pat. No. 9,672,715, which is a continuation of application No. 14/676,104, filed on Apr. 1, 2015, now Pat. No. 9,420,083, which is a continuation of application No. 14/271,412, filed on May 6, 2014, now Pat. No. 9,031,812, which is a continuation-in-part of application No. 14/192,282, filed on Feb. 27, 2014, now Pat. No. 9,310,909.

(51) Int. Cl.

| | | |
|---|---|---|
| A61B 5/11 | (2006.01) | |
| A63B 24/00 | (2006.01) | |
| G01C 22/00 | (2006.01) | |
| G06F 3/041 | (2006.01) | |
| G06F 15/00 | (2006.01) | |
| G08B 3/10 | (2006.01) | |
| G08B 5/36 | (2006.01) | |
| G08B 6/00 | (2006.01) | |
| G08B 21/04 | (2006.01) | |
| G08B 21/18 | (2006.01) | |
| G16H 20/30 | (2018.01) | |
| G16H 20/40 | (2018.01) | |
| G16H 40/63 | (2018.01) | |
| G16H 40/67 | (2018.01) | |
| G16Z 99/00 | (2019.01) | |
| H04L 12/18 | (2006.01) | |
| H04L 51/52 | (2022.01) | |
| H04L 65/403 | (2022.01) | |
| H04L 67/1095 | (2022.01) | |
| H04L 67/12 | (2022.01) | |
| H04L 67/56 | (2022.01) | |
| H04M 1/724 | (2021.01) | |
| H04M 1/72451 | (2021.01) | |
| H04M 1/72454 | (2021.01) | |
| H04W 4/00 | (2018.01) | |
| A61B 5/0205 | (2006.01) | |
| A61B 5/021 | (2006.01) | |
| A61B 5/024 | (2006.01) | |
| A61B 5/1455 | (2006.01) | |
| A61B 5/22 | (2006.01) | |
| H04L 51/58 | (2022.01) | |

(52) U.S. Cl.
CPC ............ *A61B 5/1118* (2013.01); *A61B 5/112* (2013.01); *A61B 5/4809* (2013.01); *A61B 5/486* (2013.01); *A61B 5/4866* (2013.01); *A61B 5/7264* (2013.01); *A61B 5/7405* (2013.01); *A61B 5/743* (2013.01); *A61B 5/7435* (2013.01); *A61B 5/7455* (2013.01); *A61B 5/746* (2013.01); *A63B 24/0062* (2013.01); *G01C 22/006* (2013.01); *G06F 3/041* (2013.01); *G06F 15/00* (2013.01); *G08B 3/10* (2013.01); *G08B 5/36* (2013.01); *G08B 6/00* (2013.01); *G08B 21/182* (2013.01); *G16H 20/30* (2018.01); *G16H 20/40* (2018.01); *G16H 40/63* (2018.01); *G16H 40/67* (2018.01); *G16Z 99/00* (2019.02); *H04L 12/1895* (2013.01); *H04L 51/52* (2022.05); *H04L 65/403* (2013.01); *H04L 67/1095* (2013.01); *H04L 67/12* (2013.01); *H04L 67/56* (2022.05); *H04M 1/724* (2021.01); *H04M 1/72451* (2021.01); *H04M 1/72454* (2021.01); *H04W 4/00* (2013.01); *A61B 5/02055* (2013.01); *A61B 5/021* (2013.01); *A61B 5/024* (2013.01); *A61B 5/02405* (2013.01); *A61B 5/1123* (2013.01); *A61B 5/14551* (2013.01); *A61B 5/222* (2013.01); *A61B 5/4812* (2013.01); *A61B 5/4815* (2013.01); *A61B 5/681* (2013.01); *A61B 5/6838* (2013.01); *A61B 2560/0214* (2013.01); *A61B 2560/0242* (2013.01); *A61B 2562/0219* (2013.01); *H04L 51/58* (2022.05)

(58) Field of Classification Search
CPC ..... A61B 5/1112; A61B 5/1118; A61B 5/112; A61B 5/4809; A61B 5/486; A61B 5/4866; A61B 5/7264; A61B 5/7405; A61B 5/743; A61B 5/7435; A61B 5/7455; A61B 5/746; A61B 5/02055; A61B 5/021; A61B 5/024; A61B 5/02405; A61B 5/1123; A61B 5/14551; A61B 5/222; A61B 5/4812; A61B 5/4815; A61B 5/681; A61B 5/6838; A61B 2560/0242; A61B 2562/0219; A63B 24/0062; G01C 22/006; G06F 3/041; G06F 15/00; G16H 20/30; G16H 20/40; G16H 40/63; G16H 40/67; G16Z 99/00; H04L 12/1895; H04L 51/32; H04L 65/403; H04L 67/1095; H04L 67/12; H04L 67/28; H04L 51/38; H04L 67/22; H04M 1/724; H04M 1/72451; H04M 1/72454; H04W 4/00; H04W 4/029
See application file for complete search history.

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Walter |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,938,228 A | 7/1990 | Righter et al. |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,323,650 A | 6/1994 | Fullen et al. |
| 5,339,294 A | 8/1994 | Rodgers |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,612,931 A | 3/1997 | Sato et al. |
| 5,645,509 A | 7/1997 | Brewer et al. |
| 5,671,162 A | 9/1997 | Werbin |
| 5,704,350 A | 1/1998 | Williams, III |
| 5,724,265 A | 3/1998 | Hutchings |
| 5,876,350 A | 3/1999 | Lo et al. |
| 5,890,128 A | 3/1999 | Diaz et al. |

(56) References Cited

U.S. PATENT DOCUMENTS

| | | |
|---|---|---|
| 5,891,042 A | 4/1999 | Sham et al. |
| 5,894,454 A | 4/1999 | Kondo |
| 5,899,963 A | 5/1999 | Hutchings |
| 5,946,274 A | 8/1999 | Yamaguchi et al. |
| 5,947,868 A | 9/1999 | Dugan |
| 5,955,667 A | 9/1999 | Fyfe |
| 5,976,083 A | 11/1999 | Richardson et al. |
| 5,978,923 A | 11/1999 | Kou |
| 6,018,705 A | 1/2000 | Gaudet et al. |
| 6,077,193 A | 6/2000 | Buhler et al. |
| 6,085,248 A | 7/2000 | Sambamurtby et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,300,947 B1 | 10/2001 | Kanevsky |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenbaus et al. |
| 6,469,718 B1 | 10/2002 | Setogawa et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,583,369 B2 | 6/2003 | Montagnino et al. |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 6,888,927 B1 | 5/2005 | Cruickshank et al. |
| 7,041,032 B1 | 5/2006 | Calvano |
| 7,062,225 B2 | 6/2006 | White |
| 7,133,690 B2 | 11/2006 | Ranta-Aho et al. |
| 7,155,729 B1 | 12/2006 | Andrew et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,254,516 B2 | 8/2007 | Case, Jr. et al. |
| 7,261,690 B2 | 8/2007 | Teller et al. |
| 7,272,982 B2 | 9/2007 | Neuhauser et al. |
| 7,285,090 B2 | 10/2007 | Stivoric et al. |
| 7,334,472 B2 | 2/2008 | Seo et al. |
| 7,373,820 B1 | 5/2008 | James |
| 7,443,292 B2 | 10/2008 | Jensen et al. |
| 7,457,724 B2 | 11/2008 | Vock et al. |
| 7,458,014 B1 | 11/2008 | Rubin et al. |
| 7,467,060 B2 | 12/2008 | Kulach et al. |
| 7,499,439 B2 | 3/2009 | Li et al. |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,653,508 B1 | 1/2010 | Kahn et al. |
| 7,662,065 B1 | 2/2010 | Kahn et al. |
| 7,690,556 B1 | 4/2010 | Kahn et al. |
| 7,713,173 B2 | 5/2010 | Shin et al. |
| 7,717,866 B2 | 5/2010 | Damen |
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,793,361 B2 | 9/2010 | Ishihara et al. |
| 7,805,150 B2 * | 9/2010 | Graham .............. G06F 16/2365 |
| | | 701/472 |
| 7,881,902 B1 | 2/2011 | Kahn et al. |
| 7,913,185 B1 | 3/2011 | Benson et al. |
| 7,927,253 B2 | 4/2011 | Vincent et al. |
| 7,983,876 B2 | 7/2011 | Vock et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,132,037 B2 | 3/2012 | Fehr et al. |
| 8,162,804 B2 | 4/2012 | Tagliabue |
| 8,172,761 B1 | 5/2012 | Rulkov et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,270,297 B2 | 9/2012 | Akasaka et al. |
| 8,306,508 B1 | 11/2012 | Lundy et al. |
| 8,311,769 B2 | 11/2012 | Yuen et al. |
| 8,311,770 B2 | 11/2012 | Yuen et al. |
| 8,365,073 B2 | 1/2013 | Kim et al. |
| 8,386,008 B2 | 2/2013 | Yuen et al. |
| 8,437,980 B2 | 5/2013 | Yuen et al. |
| 8,441,356 B1 | 5/2013 | Tedesco et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,600,457 B2 | 12/2013 | Vargas et al. |
| 8,615,377 B1 * | 12/2013 | Yuen ..................... A61B 5/222 |
| | | 702/160 |
| 8,630,741 B1 | 1/2014 | Matsuoka et al. |
| 8,634,796 B2 | 1/2014 | Johnson |
| 8,670,953 B2 | 3/2014 | Yuen et al. |
| 8,684,900 B2 | 4/2014 | Tran |
| 8,690,578 B1 | 4/2014 | Nusbaum et al. |
| 8,734,296 B1 * | 5/2014 | Brumback ........... A61B 5/7282 |
| | | 702/19 |
| 8,738,321 B2 | 5/2014 | Yuen et al. |
| 8,738,323 B2 | 5/2014 | Yuen et al. |
| 8,744,803 B2 | 6/2014 | Park et al. |
| 8,762,101 B2 | 6/2014 | Yuen et al. |
| 8,764,651 B2 | 7/2014 | Tran |
| 8,784,271 B2 | 7/2014 | Brumback et al. |
| 8,787,006 B2 | 7/2014 | Golko et al. |
| 8,847,988 B2 | 9/2014 | Geisner et al. |
| 8,896,526 B1 | 11/2014 | Park |
| 8,903,671 B2 | 12/2014 | Park et al. |
| 8,944,958 B1 | 2/2015 | Brumback et al. |
| 8,947,239 B1 | 2/2015 | Park |
| 8,968,195 B2 | 3/2015 | Tran |
| 9,017,221 B2 | 4/2015 | Brumback et al. |
| 9,026,927 B2 | 5/2015 | Brumback et al. |
| 9,031,812 B2 | 5/2015 | Roberts |
| 9,050,488 B2 | 6/2015 | Brumback et al. |
| 9,098,991 B2 | 8/2015 | Park et al. |
| 9,286,789 B2 | 3/2016 | Park et al. |
| 9,288,298 B2 | 3/2016 | Choudhary |
| 9,310,909 B2 | 4/2016 | Myers et al. |
| 9,344,546 B2 | 5/2016 | Choudhary et al. |
| 9,383,820 B2 | 7/2016 | Fleizach et al. |
| 9,389,057 B2 * | 7/2016 | Meschter ............... G16H 50/70 |
| 9,409,052 B2 * | 8/2016 | Werner ................... G09B 5/02 |
| 9,420,083 B2 | 8/2016 | Roberts |
| 9,600,994 B2 | 3/2017 | Park et al. |
| 9,610,047 B2 | 4/2017 | Brumback et al. |
| 9,641,469 B2 | 5/2017 | Choudhary et al. |

(56) References Cited

U.S. PATENT DOCUMENTS

| | | |
|---|---|---|
| 9,672,715 B2 | 6/2017 | Roberts et al. |
| 9,773,396 B2 | 9/2017 | Park et al. |
| 9,965,059 B2 | 5/2018 | Myers et al. |
| 10,109,175 B2 | 10/2018 | Roberts et al. |
| 10,135,934 B2 | 11/2018 | Park et al. |
| 10,796,549 B2 * | 10/2020 | Roberts .............. A61B 5/486 |
| 11,521,474 B2 * | 12/2022 | Roberts .............. G16H 40/63 |
| 2001/0002122 A1 | 5/2001 | Vong et al. |
| 2001/0049470 A1 | 12/2001 | Mault |
| 2001/0055242 A1 | 12/2001 | Deshmukh et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0161644 A1 | 10/2002 | Duffield |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0059790 A1 | 3/2004 | Austin-Lane et al. |
| 2004/0061324 A1 | 4/2004 | Howard |
| 2004/0117963 A1 | 6/2004 | Schneider |
| 2004/0127198 A1 | 7/2004 | Roskind et al. |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2005/0037844 A1 | 2/2005 | Shum et al. |
| 2005/0038679 A1 | 2/2005 | Short |
| 2005/0272564 A1 | 2/2005 | Pyles et al. |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0115561 A1 | 6/2005 | Stahmann et al. |
| 2005/0163056 A1 | 7/2005 | Ranta-Aho et al. |
| 2005/0171410 A1 | 8/2005 | Hjelt et al. |
| 2005/0228244 A1 | 10/2005 | Banet |
| 2005/0228692 A1 | 10/2005 | Hodgdon |
| 2005/0234742 A1 | 10/2005 | Hodgdon |
| 2005/0245793 A1 | 11/2005 | Hilton et al. |
| 2005/0248718 A1 | 11/2005 | Howell et al. |
| 2005/0250551 A1 | 11/2005 | Helle |
| 2006/0020174 A1 | 1/2006 | Matsumura et al. |
| 2006/0020177 A1 | 1/2006 | Seo et al. |
| 2006/0025282 A1 | 2/2006 | Redmann |
| 2006/0028429 A1 | 2/2006 | Kanevsky et al. |
| 2006/0036642 A1 | 2/2006 | Horvitz et al. |
| 2006/0047208 A1 | 3/2006 | Yoon |
| 2006/0047447 A1 | 3/2006 | Brady et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0090139 A1 | 4/2006 | Jenni et al. |
| 2006/0111944 A1 | 5/2006 | Sirmans, Jr. |
| 2006/0129436 A1 | 6/2006 | Short |
| 2006/0143645 A1 | 6/2006 | Vock et al. |
| 2006/0217231 A1 | 9/2006 | Parks et al. |
| 2006/0242590 A1 | 10/2006 | Polivy et al. |
| 2006/0247952 A1 | 11/2006 | Muraca |
| 2006/0259537 A1 | 11/2006 | Emberton et al. |
| 2006/0277100 A1 | 12/2006 | Parham |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2006/0293041 A1 | 12/2006 | Kim |
| 2007/0049836 A1 | 3/2007 | Chen |
| 2007/0050715 A1 | 3/2007 | Behar |
| 2007/0051369 A1 | 3/2007 | Choi et al. |
| 2007/0071643 A1 | 3/2007 | Hall et al. |
| 2007/0072156 A1 | 3/2007 | Kaufman et al. |
| 2007/0083602 A1 | 4/2007 | Heggenhougen et al. |
| 2007/0118043 A1 | 5/2007 | Oliver et al. |
| 2007/0123391 A1 | 5/2007 | Shin et al. |
| 2007/0136093 A1 | 6/2007 | Rankin et al. |
| 2007/0143068 A1 | 6/2007 | Pasolini et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0173327 A1 | 7/2007 | Kilgore et al. |
| 2007/0179356 A1 | 8/2007 | Wessel |
| 2007/0188468 A1 | 8/2007 | Lee et al. |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0219059 A1 | 9/2007 | Schwartz et al. |
| 2007/0276271 A1 | 11/2007 | Chan |
| 2007/0293371 A1 | 12/2007 | Hilfiker et al. |
| 2008/0070603 A1 | 3/2008 | Mao |
| 2008/0084823 A1 | 4/2008 | Akasaka et al. |
| 2008/0093838 A1 | 4/2008 | Tropper et al. |
| 2008/0096726 A1 | 4/2008 | Riley |
| 2008/0097550 A1 | 4/2008 | Dicks et al. |
| 2008/0114829 A1 | 5/2008 | Button et al. |
| 2008/0125288 A1 | 5/2008 | Case |
| 2008/0129457 A1 | 6/2008 | Ritter et al. |
| 2008/0134102 A1 | 6/2008 | Movold et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0155455 A1 | 6/2008 | Balasubramanian |
| 2008/0157956 A1 | 7/2008 | Radivojevic et al. |
| 2008/0176655 A1 | 7/2008 | James et al. |
| 2008/0191885 A1 | 8/2008 | Loree, IV et al. |
| 2008/0200312 A1 | 8/2008 | Tagliabue |
| 2008/0243432 A1 | 10/2008 | Kato et al. |
| 2008/0249736 A1 | 10/2008 | Prstojevich |
| 2008/0269625 A1 | 10/2008 | Halperin et al. |
| 2008/0287751 A1 | 11/2008 | Stivoric et al. |
| 2008/0301250 A1 | 12/2008 | Hardy et al. |
| 2008/0319330 A1 | 12/2008 | Juntunen et al. |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0048070 A1 | 2/2009 | Vincent et al. |
| 2009/0054737 A1 | 2/2009 | Magar et al. |
| 2009/0063193 A1 | 3/2009 | Barton et al. |
| 2009/0085865 A1 | 4/2009 | Fattah |
| 2009/0098821 A1 | 4/2009 | Shinya |
| 2009/0105047 A1 | 4/2009 | Guidi et al. |
| 2009/0106641 A1 | 4/2009 | Shinn |
| 2009/0125917 A1 | 5/2009 | Parker et al. |
| 2009/0150178 A1 | 6/2009 | Sutton et al. |
| 2009/0156172 A1 | 6/2009 | Chan |
| 2009/0167542 A1 | 7/2009 | Culbert et al. |
| 2009/0171788 A1 | 7/2009 | Tropper et al. |
| 2009/0184849 A1 | 7/2009 | Nasiri |
| 2009/0192391 A1 | 7/2009 | Lovitt et al. |
| 2009/0195350 A1 | 8/2009 | Tsern et al. |
| 2009/0195497 A1 | 8/2009 | Fitzgerald et al. |
| 2009/0221403 A1 | 9/2009 | Chan et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0305732 A1 | 12/2009 | Marcellino et al. |
| 2009/0305744 A1 | 12/2009 | Ullrich |
| 2009/0307517 A1 | 12/2009 | Fehr et al. |
| 2009/0307619 A1 | 12/2009 | Gupta et al. |
| 2009/0309742 A1 | 12/2009 | Alexander et al. |
| 2009/0320047 A1 | 12/2009 | Khan et al. |
| 2010/0015584 A1 | 1/2010 | Singer et al. |
| 2010/0024531 A1 | 2/2010 | Senoo |
| 2010/0059561 A1 | 3/2010 | Ellis et al. |
| 2010/0069203 A1 | 3/2010 | Kawaguchi et al. |
| 2010/0076278 A1 | 3/2010 | van der Zande et al. |
| 2010/0085841 A1 | 4/2010 | Lazaridis et al. |
| 2010/0105525 A1 | 4/2010 | Thukral et al. |
| 2010/0159709 A1 | 6/2010 | Kotani et al. |

(56) References Cited

U.S. PATENT DOCUMENTS

| | | |
|---|---|---|
| 2010/0159995 A1 | 6/2010 | Stallings et al. |
| 2010/0167783 A1 | 7/2010 | Alameh et al. |
| 2010/0185064 A1 | 7/2010 | Bandic et al. |
| 2010/0188328 A1 | 7/2010 | Dodge et al. |
| 2010/0205541 A1 | 8/2010 | Rapaport et al. |
| 2010/0210975 A1 | 8/2010 | Anthony, III et al. |
| 2010/0217099 A1 | 8/2010 | LeBoeuf et al. |
| 2010/0240458 A1 | 9/2010 | Gaiba |
| 2010/0245078 A1 | 9/2010 | Nadkarni et al. |
| 2010/0261987 A1 | 10/2010 | Kamath |
| 2010/0295684 A1 | 11/2010 | Hsieh et al. |
| 2010/0331145 A1 | 12/2010 | Lakovic et al. |
| 2010/0331147 A1 | 12/2010 | Mikan et al. |
| 2011/0003665 A1 | 1/2011 | Burton et al. |
| 2011/0009051 A1 | 1/2011 | Khedouri et al. |
| 2011/0010617 A1 | 1/2011 | Kim et al. |
| 2011/0022349 A1 | 1/2011 | Stirling et al. |
| 2011/0032105 A1 | 2/2011 | Hoffman et al. |
| 2011/0080349 A1 | 4/2011 | Holbein et al. |
| 2011/0082007 A1 | 4/2011 | Birrell et al. |
| 2011/0087076 A1 | 4/2011 | Brynelsen et al. |
| 2011/0092282 A1 | 4/2011 | Gary |
| 2011/0106449 A1 | 5/2011 | Chowdhary et al. |
| 2011/0109540 A1 | 5/2011 | Milne et al. |
| 2011/0131005 A1 | 6/2011 | Ueshima et al. |
| 2011/0152696 A1 | 6/2011 | Ryan |
| 2011/0154196 A1 | 6/2011 | Icho et al. |
| 2011/0193704 A1 | 8/2011 | Harper et al. |
| 2011/0197157 A1 | 8/2011 | Hoffman et al. |
| 2011/0213473 A1 | 9/2011 | Vitolo et al. |
| 2011/0224508 A1 | 9/2011 | Moon |
| 2011/0230729 A1 | 9/2011 | Shirasaki et al. |
| 2011/0242043 A1 | 10/2011 | Yarvis et al. |
| 2011/0252362 A1 | 10/2011 | Cho et al. |
| 2011/0261079 A1 | 10/2011 | Ingrassia |
| 2011/0267196 A1 | 11/2011 | Hu et al. |
| 2012/0010478 A1 | 1/2012 | Kinnunen et al. |
| 2012/0010822 A1 | 1/2012 | Kato et al. |
| 2012/0015778 A1 | 1/2012 | Lee |
| 2012/0015779 A1 | 1/2012 | Powch |
| 2012/0041767 A1 | 2/2012 | Hoffman et al. |
| 2012/0059664 A1 | 3/2012 | Georgiev et al. |
| 2012/0060123 A1 | 3/2012 | Smith |
| 2012/0072165 A1 | 3/2012 | Jallon |
| 2012/0077641 A1 | 3/2012 | Dyer et al. |
| 2012/0078127 A1 | 3/2012 | McDonald et al. |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0092383 A1 | 4/2012 | Hysek et al. |
| 2012/0094649 A1 | 4/2012 | Porrati et al. |
| 2012/0108215 A1 | 5/2012 | Kameli |
| 2012/0112908 A1 | 5/2012 | Prykari et al. |
| 2012/0116550 A1 | 5/2012 | Hoffman et al. |
| 2012/0119911 A1 | 5/2012 | Jean et al. |
| 2012/0129138 A1 | 5/2012 | Redmann |
| 2012/0159218 A1 | 6/2012 | Vangala et al. |
| 2012/0165684 A1 | 6/2012 | Sholder |
| 2012/0166257 A1 | 6/2012 | Shiragami et al. |
| 2012/0183939 A1 | 7/2012 | Aragones et al. |
| 2012/0197986 A1 | 8/2012 | Chen |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0246246 A1 | 9/2012 | Moore |
| 2012/0252416 A1 | 10/2012 | Kissinger et al. |
| 2012/0253485 A1 | 10/2012 | Weast et al. |
| 2012/0258433 A1 | 10/2012 | Hope et al. |
| 2012/0265480 A1 | 10/2012 | Oshima |
| 2012/0274508 A1 | 11/2012 | Brown et al. |
| 2012/0277605 A1 | 11/2012 | Colborn |
| 2012/0277891 A1 | 11/2012 | Aragones |
| 2012/0283855 A1 | 11/2012 | Hoffman |
| 2012/0290109 A1 | 11/2012 | Engelberg |
| 2012/0291544 A1 | 11/2012 | Kawabe |
| 2012/0295676 A1 | 11/2012 | Ackerson |
| 2012/0303319 A1 | 11/2012 | Kirkeby |
| 2012/0316406 A1 | 12/2012 | Rahman et al. |
| 2012/0316456 A1 | 12/2012 | Rahman et al. |
| 2012/0316896 A1 | 12/2012 | Rahman et al. |
| 2012/0324226 A1 | 12/2012 | Bichsel et al. |
| 2012/0326873 A1 | 12/2012 | Utter, II |
| 2012/0330109 A1 | 12/2012 | Tran |
| 2013/0006718 A1 | 1/2013 | Nielsen et al. |
| 2013/0007665 A1 | 1/2013 | Chaudhri et al. |
| 2013/0013331 A1 | 1/2013 | Horseman |
| 2013/0017891 A1 | 1/2013 | Romero et al. |
| 2013/0041590 A1 | 2/2013 | Burich et al. |
| 2013/0067014 A1 | 3/2013 | Lau et al. |
| 2013/0072169 A1 | 3/2013 | Ross et al. |
| 2013/0072823 A1 | 3/2013 | Kahn et al. |
| 2013/0073254 A1 | 3/2013 | Yuen et al. |
| 2013/0073255 A1 | 3/2013 | Yuen et al. |
| 2013/0078958 A1 | 3/2013 | Kyprianou |
| 2013/0080113 A1 | 3/2013 | Yuen et al. |
| 2013/0080811 A1 | 3/2013 | Low et al. |
| 2013/0090881 A1 | 4/2013 | Janardhanan et al. |
| 2013/0095459 A1 | 4/2013 | Tran |
| 2013/0096843 A1 | 4/2013 | Yuen et al. |
| 2013/0106603 A1 | 5/2013 | Weast et al. |
| 2013/0106684 A1 | 5/2013 | Weast et al. |
| 2013/0114415 A1 | 5/2013 | Das et al. |
| 2013/0117381 A1 | 5/2013 | Garcia et al. |
| 2013/0119255 A1 | 5/2013 | Dickinson et al. |
| 2013/0122928 A1 | 5/2013 | Pfluger |
| 2013/0123959 A1 | 5/2013 | Kan et al. |
| 2013/0138734 A1 | 5/2013 | Crivello et al. |
| 2013/0151196 A1 | 6/2013 | Yuen et al. |
| 2013/0157646 A1 | 6/2013 | Ferren et al. |
| 2013/0158369 A1 | 6/2013 | Yuen et al. |
| 2013/0166048 A1 | 6/2013 | Werner et al. |
| 2013/0178334 A1 | 7/2013 | Brammer |
| 2013/0190903 A1 | 7/2013 | Balakrishnan et al. |
| 2013/0191034 A1 | 7/2013 | Weast et al. |
| 2013/0197681 A1 | 8/2013 | Alberth, Jr. et al. |
| 2013/0198685 A1 | 8/2013 | Bernini et al. |
| 2013/0203475 A1 | 8/2013 | Kil |
| 2013/0205306 A1 | 8/2013 | Kelly |
| 2013/0228063 A1 | 9/2013 | Turner |
| 2013/0231574 A1 | 9/2013 | Tran |
| 2013/0234924 A1 | 9/2013 | Janefalkar et al. |
| 2013/0237874 A1 | 9/2013 | Zoicas |
| 2013/0238287 A1 | 9/2013 | Hoffman et al. |
| 2013/0241718 A1 | 9/2013 | Wang et al. |
| 2013/0254525 A1 | 9/2013 | Johnson et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0271392 A1 | 10/2013 | Lyons |
| 2013/0274904 A1 | 10/2013 | Coza et al. |
| 2013/0289366 A1 | 10/2013 | Chua et al. |
| 2013/0290879 A1 | 10/2013 | Greisson |
| 2013/0293494 A1 | 11/2013 | Reshef |
| 2013/0296666 A1 | 11/2013 | Kumar et al. |
| 2013/0296672 A1 | 11/2013 | O'Neil et al. |
| 2013/0296673 A1 | 11/2013 | Thaveeprungsriporn et al. |
| 2013/0303087 A1 | 11/2013 | Hauser et al. |
| 2013/0310896 A1 | 11/2013 | Mass |
| 2013/0324368 A1 | 12/2013 | Aragones et al. |
| 2013/0325396 A1 | 12/2013 | Yuen et al. |
| 2013/0325491 A1 | 12/2013 | Ferrari |
| 2013/0337974 A1 | 12/2013 | Yanev et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0052280 A1 | 2/2014 | Yuen et al. |
| 2014/0066816 A1 | 3/2014 | McNames et al. |

(56) References Cited

U.S. PATENT DOCUMENTS

| | | |
|---|---|---|
| 2014/0067278 A1 | 3/2014 | Yuen et al. |
| 2014/0070957 A1 | 3/2014 | Longinotti-Buitoni et al. |
| 2014/0077673 A1 | 3/2014 | Garg et al. |
| 2014/0081667 A1 | 3/2014 | Joao |
| 2014/0094941 A1 | 4/2014 | Ellis et al. |
| 2014/0099614 A1 | 4/2014 | Hu et al. |
| 2014/0125618 A1 | 5/2014 | Panther et al. |
| 2014/0143064 A1 | 5/2014 | Tran |
| 2014/0143737 A1 | 5/2014 | Mistry et al. |
| 2014/0164611 A1 | 6/2014 | Molettiere et al. |
| 2014/0169675 A1 | 6/2014 | King et al. |
| 2014/0176335 A1 | 6/2014 | Brumback et al. |
| 2014/0176346 A1 | 6/2014 | Brumback et al. |
| 2014/0176422 A1 | 6/2014 | Brumback et al. |
| 2014/0180022 A1 | 6/2014 | Stivoric et al. |
| 2014/0180595 A1 | 6/2014 | Brumback et al. |
| 2014/0197946 A1 | 7/2014 | Park et al. |
| 2014/0197963 A1 | 7/2014 | Park et al. |
| 2014/0197965 A1 | 7/2014 | Park et al. |
| 2014/0213858 A1 | 7/2014 | Presura et al. |
| 2014/0240122 A1 | 8/2014 | Roberts et al. |
| 2014/0249393 A1 | 9/2014 | Proud |
| 2014/0275885 A1 | 9/2014 | Isaacson et al. |
| 2014/0278229 A1 | 9/2014 | Hong et al. |
| 2014/0316305 A1 | 10/2014 | Venkatraman et al. |
| 2015/0026647 A1 | 1/2015 | Park et al. |
| 2015/0042471 A1 | 2/2015 | Park et al. |
| 2015/0081465 A1 | 3/2015 | Dyment |
| 2015/0091812 A1 | 4/2015 | Sood et al. |
| 2015/0094831 A1 | 4/2015 | Brumback et al. |
| 2015/0094832 A1 | 4/2015 | Brumback et al. |
| 2015/0181314 A1 | 6/2015 | Swanson |
| 2015/0207915 A1 | 7/2015 | Roberts et al. |
| 2015/0231446 A1 | 8/2015 | Brumback et al. |
| 2015/0245801 A1 | 9/2015 | Brumback et al. |
| 2015/0262499 A1 | 9/2015 | Wicka |
| 2015/0294554 A1 | 10/2015 | Park et al. |
| 2016/0267764 A1 | 9/2016 | Park et al. |
| 2016/0314670 A1 | 10/2016 | Roberts et al. |
| 2017/0143239 A1 | 5/2017 | Park et al. |
| 2017/0237694 A1 | 8/2017 | Choudhary |
| 2017/0270765 A1 | 9/2017 | Roberts et al. |
| 2019/0057593 A1 | 2/2019 | Park et al. |

FOREIGN PATENT DOCUMENTS

| | | |
|---|---|---|
| CN | 101779953 A | 7/2010 |
| CN | 101785675 A | 7/2010 |
| CN | 101843492 A | 9/2010 |
| CN | 101918950 A | 12/2010 |
| CN | 102068261 A | 5/2011 |
| CN | 202282004 U | 6/2012 |
| CN | 102598086 | 7/2012 |
| CN | 102930490 A | 2/2013 |
| CN | 103269407 A | 8/2013 |
| EP | 1 721 237 | 8/2012 |
| JP | 11-347021 | 12/1999 |
| RU | 2178588 | 1/2002 |
| WO | WO 02/011019 | 2/2002 |
| WO | WO 06/055125 | 5/2006 |
| WO | WO 06/090197 | 8/2006 |
| WO | WO 2007/143535 | 12/2007 |
| WO | WO 08/038141 | 4/2008 |
| WO | WO 09/042965 | 4/2009 |
| WO | WO 2011/028383 | 3/2011 |
| WO | WO 2011/139671 | 11/2011 |
| WO | WO 12/170586 | 12/2012 |
| WO | WO 12/170924 | 12/2012 |
| WO | WO 12/171032 | 12/2012 |
| WO | WO 2012/170366 | 12/2012 |
| WO | WO 2013/040674 | 3/2013 |
| WO | WO 2013/093011 | 6/2013 |
| WO | WO 2013/169755 | 11/2013 |
| WO | WO 15/127067 | 8/2015 |
| WO | WO 16/003269 | 1/2016 |

OTHER PUBLICATIONS

Ali-Hasan et al., "Fitster: Social Fitness Information Visualizer," Extended Abstracts on Human Factors in Computing Systems, Association for Computing Machinery Press, Apr. 2006, pp. 1795-1800.

Anderson, et al., "Shakra: Tracking and Sharing Daily Activity Levels with Unaugmented Mobile Phones," Mobile Networks Application, vol. 12, Aug. 3, 2007, pp. 185-199.

Bonato, "Wearable Sensors and Systems. From Enabling Technology to Clinical Applications", Institute of Electrical and Electronics Engineers Engineering in Medicine and Biology Magazine: the quarterly magazine of the Engineering in Medicine & Biology Society, vol. 29, Issue 3, 2010, pp. 25-36.

Buttussi et al., "Mopet, A Context-Aware and User-Adaptive Wearable System for Fitness Training", Artificial Intelligence in Medicine, vol. 42, No. 2, 2008, pp. 153-163.

Chandrasekar et al., "Plug-and-Play, Single-Cip Photoplethysmography", 34th Annual International Conference of the Institute of Electrical and Electronics Engineers Engineering in Medicine and Biology Society, San Diego, California, United States, Aug. 28-Sep. 1, 2012, 4 pages.

Chinese First Office Action dated Oct. 20, 2015, issued in CN 201410475447.4 [FTBTP005CN].

Chinese First Office Action dated May 3, 2016, issued in CN 201310741076.5 [FTBTP003CN].

Chinese First Office Action dated Nov. 28, 2016 issued in CN 201410475446.X [FTBTP006CN].

Chinese Second Office Action dated May 19, 2016, issued in CN 201410475447.4 [FTBTP005CN].

Chinese Second Office Action dated Dec. 1, 2016, issued in CN 201310741076.5 [FTBTP003CN].

Chinese Second Office Action dated May 31, 2017, issued in CN 201410475446.X [FTBTP006CN].

Chinese Third Office Action dated Oct. 26, 2016, issued in CN 201410475447.4 [FTBTP005CN].

Chinese Third Office Action dated May 4, 2017, issued in CN 201310741076.5 [FTBTP003CN].

Chudnow. "Basis Wristband Make its Debut", The Wired Self, Living in a Wired World, published in Health [retrieved on thewiredself.com/health/basis-wrist-band-make-its-debut], 3 pages.

Consolvo et al., "Design Requirements for Technologies That Encourage Physical Activity," 2006 Conference on Human Factors in Computing Systems, 2006, pp. 457-466.

Desmarais, "Which New Activity Tracker is Best for You?", Health and Home, Health & Fitness, Guides & Reviews, [Retrieved on Sep. 23, 2013, at http://www.techlicious.com/guide/which-new-activity-tracker-is-right-for-you], 4 pages.

Empson, "Basis Reveals an Awesome New Affordable Heart and Health Tracker You Can Wear on Your Wrist", [retrieved on Sep. 23, 2013, at http://techcrunch.com/2011/09/22/basis-reveals-an-awesome-new . . . ], 3 pages.

Fang et al., "Design of a Wireless Assisted Pedestrian Dead Reckoning System—The NavMote Experience", Institute of Electrical and Electronics Engineers Transactions on Instrumentation and Measurement, vol. 54, No. 6, Dec. 2005, pp. 2342-2358.

Fitbit User's Manual, Last Updated Oct. 22, 2009, 15 pages.

Forerunner.RTM. 10 Owner's Manual, Aug. 2012, Garmin Ltd., 10 pages.

Forerunner RTM. 110 Owner's Manual, 2010, "GPS-Enabled Sport Watch," Garmin Ltd., 16 pages.

Forerunner.RTM. 201 Personal Trainer Owner's Manual, Feb. 2006, Garmin Ltd., 48 pages.

Forerunner.RTM. 205/305 Owner's Manual, GPS-Enabled Trainer for Runners, 2006-2008, Garmin Ltd., 80 pages.

Forerunner.RTM. 210 Owner's Manual, "GPS-Enabled Sport Watch," Garmin Ltd., 2010, 28 pages.

Forerunner.RTM. 301 Personal Trainer Owner's Manual, Feb. 2006, Garmin Ltd., 66 pages.

Forerunner.RTM. 310XT Owner's Manual, Multisport GPS Training Device, 2009-2013, Garmin Ltd., 56 pages.

(56) References Cited

OTHER PUBLICATIONS

Forerunner.RTM. 405 Owner's Manual, Mar. 2011, "GPS-Enabled Sport Watch with Wireless Sync," Garmin Ltd., 56 pages.
Forerunner.RTM. 405CX Owner's Manual, "GPS-Enabled Sports Watch with Wireless Sync," Mar. 2009, Garmin Ltd., 56 pages.
Forerunner RTM. 410 Owner's Manual, Jul. 2012, "GPS-Enabled Sport Watch with Wireless Sync," Garmin Ltd., 52 pages.
Forerunner.RTM. 50 with ANT+Sport.TM. Wireless Technology, Owner's Manual, Nov. 2007, Garmin Ltd., 44 pages.
Forerunner.RTM. 910XT Owner's Manual, Jan. 2013, Garmin Ltd., 56 pages.
Gamelin et al., "Validity of The Polar S810 Heart Rate Monitor to Measure R-R Intervals at Rest." Medical Science Sports Exercise vol. 38, No. 5, 2006, pp. 887-893.
Garmin Swim. TM. Owner's Manual, Jun. 2012, 12 pages.
Godfrey et al., "Direct Measurement of Human Movement by Accelerometry", Medical Engineering & Physics, vol. 30, 2008, pp. 1364-1386.
Godha et al., "Foot Mounted Inertia System for Pedestrian Navigation", Measurement Science and Technology, vol. 19, No. 7, May 2008, pp. 1-9.
Gomes et al., "Steptacular: An Incentive Mechanism for Promoting Wellness," 2012 Fourth International Conference on Communication Systems and Networks, Bangalore, India, Jan. 3-7, 2012, pp. 1-6.
Gupta et al., "Digital Fitness Connector: Smart Wearable System," 2011 First International Conference on Informatics and Computational Intelligence, Bandung, Indonesia, Dec. 12-14, 2011, pp. 118-121.
International Search Report dated Aug. 15, 2008, in related application No. PCT/IB07/03617.
Intersema, "Using MS5534 for Altimeters and Barometers", Application Note AN501, Jan. 3, 2006, 12 pages.
Kranz et al., "The Mobile Fitness Coach: Towards Individualized Skill Assessment Using Personalized Mobile Devices", Pervasive Mobile Computing, vol. 9, Issue 2, Apr. 2013, pp. 203-215.
Ladetto et al., "On Foot Navigation: When GPS Alone is not Enough", Journal of Navigation, vol. 53, No. 2, Sep. 2000, pp. 279-285.
Lammel et al., "Indoor Navigation with MEMS Sensors", Eurosensors XIII Conference, vol. 1, No. 1, Sep. 2009, pp. 532-535.
Lane et al., "A Survey of Mobile Phone Sensing, " Institute of Electrical and Electronics Engineers Communications Magazine, vol. 48, 2010, pp. 140-150.
Lark/Larkpro, User Manual, 2012, "What's in the Box," Lark Technologies, 7 pages.
Larklife, User Manual, 2012, Lark Technologies, 7 pages.
Le Masurier et al., "Comparison of Pedometer and Accelerometer Accuracy Under Controlled Conditions," Medicine & Science in Sports & Exercise, vol. 35, 2003, pp. 867-871.
Lester et al., "A Hybrid Discriminative/Generative Approach for Modeling Human Activities", International Joint Conference on Artificial Intelligence, 2005, pp. 766-772.
Lester et al., "Validated Caloric Expenditure Estimation Using a Single Body-Worn Sensor", International Conference on Ubiquitous Computing, Sep. 2009, pp. 225-234.
Marschollek et al., "A Performance Comparison of Accelerometry-Based Step Detection Algorithms on a Large, Non-Laboratory Sample of Healthy and Mobility-Impaired Persons," Annual International Conference of the Institute of Electrical and Electronics Engineers, Engineering in EMBS Society, Vancouver, British Columbia, Canada, Engineering Medicine Biology Magazine, vol. 2008, Aug. 20-24, 2008, pp. 1319-1322.
Milošević et al., "Applications of Smartphones for Ubiquitous Health Monitoring and Wellbeing Management," Journal of Information Technology and Applications, vol. 1, Jun. 2011, pp. 7-15.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
Ohtaki et al., "Automatic Classification of Ambulatory Movements and Evaluation of Energy Consumptions Utilizing Accelerometers and Barometer", Microsystem Technologies, vol. 11, No. 8-10, Aug. 2005, pp. 1034-1040.
Parkka et al., "Activity Classification Using Realistic Data from Wearable Sensors", Institute of Electrical and Electronics Engineers Transactions on Information Technology in Biomedicine, vol. 10, No. 1, Jan. 2006, pp. 119-128.
"Parts of Your Band," (Product Release Date Unknown, Downloaded Jul. 22, 2013) Jawbone Up Band, 1 page.
Perrin et al., "Improvement of Walking Speed Prediction by Accelerometry and Altimetry, Validated by Satellite Positioning", Medical & Biological Engineering & Computing, vol. 38, 2000, pp. 164-168.
Rainmaker, "Garmin Swim Watch In-Depth Review", Feb. 16, 2013, A Survey of Mobile Phone Sensing retrieved on Sep. 9, 2013, at http://www.dcrainmaker.com/2012/06/garmin-swim-in-depth-review.html, 38 pages.
Retscher, "An Intelligent Multi-Sensor System for Pedestrian Navigation", Journal of Global Positioning Systems, vol. 5, No. 1, 2006, pp. 110-118.
Sagawa et al., "Classification of Human Moving Patterns Using Air Pressure and Acceleration", 24th Annual Conference of the Institute of Electrical and Electronics Engineers Industrial Electronics Society, vol. 2, Aug. 30, 1998, pp. 1214-1219.
Sagawa et al., "Non-Restricted Measurement of Walking Distance", Institute of Electrical and Electronics Engineers International Conference on Systems, Man, and Cybernetics, vol. 3, Oct. 2000, pp. 1847-1852.
Schneider et al., "Pedometer Measures of Free-Living Physical Activity: Comparison of 13 Models," Medicine & Science in Sports & Exercise vol. 36, No. 2, Feb. 2004, pp. 331-335.
Scp 1000-D01/D11 Pressure Sensor as Barometer and Altimeter, VTI Technologies Application, Jun. 2006, Note 33.
Specification of The Bluetooth Rtm. System, Core Package, Version 4.1, Dec. 2013, vol. 0 & 1, 282 pages.
Suunto LUMI User Guide, Jun., and Sep. 1997.
Tanigawa et al., "Drift-Free Dynamic Height Sensor Using MEMS IMU Aided by MEMS Pressure Sensor", 5th Workshop on Positioning, Navigation and Communication, Hannover, Germany, Mar. 2008, pp. 191-196.
Tudor-Locke et al., "Comparison of Pedometer and Accelerometer Measures of Free-Living Physical Activity", Medicine and Science in Sports and Exercise. Dec. 2002, vol. 34, No. 12, pp. 2045-2051.
Tudor-Locke, et al., "Evaluation of Quality of Commercial Pedometers, " Canadian Journal of Public Health, vol. 97, Supplement 1, Mar.-Apr. 2006, pp. S10-S15.
U.S. Advisory Action, dated Mar. 1, 2016, issued in U.S. Appl. No. 14/712,501.
U.S. Advisory Action, dated Nov. 17, 2014, issued in U.S. Appl. No. 14/045,574.
U.S. Applicant Initiated Interview Summary, dated Aug. 19, 2014, issued in U.S. Appl. No. 14/050,182.
U.S. Applicant Initiated Interview Summary, dated Dec. 29, 2016, issued in U.S. Appl. No. 14/712,501.
U.S. Applicant Initiated Interview Summary, dated Mar. 7, 2014, issued in U.S. Appl. No. 14/050,182.
U.S. Applicant-Initiated Interview Summary dated Mar. 11, 2014, issued in U.S. Appl. No. 14/050,166.
U.S. Examiner's Answer to Appeal Brief, dated Feb. 16, 2017, issued in U.S. Appl. No. 14/045,563.
U.S. Examiner's Answer to Appeal Brief, dated Nov. 3, 2016, issued in U.S. Appl. No. 14/029,763.
U.S. Final Office Action, dated Apr. 28, 2016, issued in U.S. Appl. No. 14/749,386.
U.S. Final Office Action, dated Apr. 8, 2014, issued in U.S. Appl. No. 14/029,760.
U.S. Final Office Action, dated Dec. 4, 2014, issued in U.S. Appl. No. 14/029,760.

(56) References Cited

OTHER PUBLICATIONS

U.S. Final Office Action, dated Feb. 24, 2017, issued in U.S. Appl. No. 14/749,386.
U.S. Final Office Action, dated Jan. 4, 2016, issued in U.S. Appl. No. 14/045,563.
U.S. Final Office Action, dated Jul. 28, 2014, issued in U.S. Appl. No. 14/045,563.
U.S. Final Office Action, dated Jul. 31, 2014, issued in U.S. Appl. No. 14/045,574.
U.S. Final Office Action, dated Jul. 8, 2015, issued in U.S. Appl. No. 14/029,763.
U.S. Final Office Action, dated May 1, 2014, issued in U.S. Appl. No. 14/050,182.
U.S. Final Office Action, dated Nov. 15. 2017, issued in U.S. Appl. No. 14/704,818.
U.S. Final Office Action, dated Nov. 24. 2015, issued in U.S. Appl. No. 14/712,501.
U.S. Final Office Action, dated Nov. 26, 2014, issued in U.S. Appl. No. 14/261,347.
U.S. Final Office Action, dated Oct. 10, 2014, issued in U.S. Appl. No. 14/261,349.
U.S. Final Office Action, dated Sep. 26, 2016, issued in U.S. Appl. No. 14/712,501.
U.S. Notice of Allowance (Corrected Notice of Allowability), dated Apr. 1, 2015, issued in U.S. Appl. No. 14/261,349.
U.S. Notice of Allowance, dated Apr. 25, 2014, issued in U.S. Appl. No. 14/045,592.
U.S. Notice of Allowance, dated Apr. 8, 2014, issued in U.S. Appl. No. 14/050,166.
U.S. Notice of Allowance, dated Apr. 8, 2015, issued in U.S. Appl. No. 14/045,574.
U.S. Notice of Allowance, dated Dec. 24. 2014, issued in U.S. Appl. No. 14/261,349.
U.S. Notice of Allowance, dated Feb. 5, 2015, issued in U.S. Appl. No. 14/261,347.
U.S. Notice of Allowance, dated Feb. 7, 2017, issued in U.S. Appl. No. 14/712,501.
U.S. Notice of Allowance, dated Jan. 14, 2015, issued in U.S. Appl. No. 14/045,574.
U.S. Notice of Allowance, dated Jul. 23, 2018, issued in U.S. Appl. No. 15/427,638.
U.S. Notice of Allowance, dated Jul. 8, 2014, issued in U.S. Appl. No. 14/062,717.
U.S. Notice of Allowance, dated Jun. 15, 2017, issued in U.S. Appl. No. 14/749,386.
U.S. Notice of Allowance, dated Mar. 24, 2015, issued in U.S. Appl. No. 14/029,760.
U.S. Notice of Allowance, dated Nov. 14, 2014, issued in U.S. Appl. No. 14/050,182.
U.S. Notice of Allowance, dated Nov. 6, 2015, issued in U.S. Appl. No. 14/524,909.
U.S. Notice of Allowance, dated Nov. 8, 2016, issued in U.S. Appl. No. 15/017,356.
U.S. Notice of Allowance, dated Sep. 5, 2014, issued in U.S. Appl. No. 14/062,717.
U.S. Office Action, dated Apr. 10. 2015, issued in U.S. Appl. No. 14/029,759.
U.S. Office Action, dated Apr. 17, 2018, issued in U.S. Appl. No. 14/704,818.
U.S. Office Action, dated Apr. 4, 2014, issued in U.S. Appl. No. 14/045,574.
U.S. Office Action, dated Aug. 14, 2015, issued in U.S. Appl. No. 14/712,501.
U.S. Office Action, dated Aug. 31, 2016, issued in U.S. Appl. No. 14/749,386.
U.S. Office Action, dated Dec. 24, 2013, issued in U.S. Appl. No. 14/050,166.
U.S. Office Action, dated Dec. 30, 2013, issued in U.S. Appl. No. 14/029,760.
U.S. Office Action, dated Feb. 12, 2015, issued in U.S. Appl. No. 14/029,763.
U.S. Office Action, dated Feb. 5, 2014, issued in U.S. Appl. No. 14/045,563.
U.S. Office Action, dated Jan. 14, 2014, issued in U.S. Appl. No. 14/050,182.
U.S. Office Action, dated Jan. 16, 2015, issued in U.S. Appl. No. 14/524,909.
U.S. Office Action, dated Jan. 8, 2014, issued in U.S. Appl. No. 14/045,592.
U.S. Office Action, dated Jul. 17, 2015, issued in U.S. Appl. No. 14/045,563.
U.S. Office Action, dated Jul. 23, 2014, issued in U.S. Appl. No. 14/029,760.
U.S. Office Action, dated Jul. 29, 2014, issued in U.S. Appl. No. 14/261,347.
U.S. Office Action, dated Jun. 20, 2014, issued in U.S. Appl. No. 14/261,347.
U.S. Office Action, dated Jun. 20, 2017, issued in U.S. Appl. No. 14/704,818.
U.S. Office Action, dated Jun. 24, 2014, issued in U.S. Appl. No. 14/261,349.
U.S. Office Action, dated Jun. 7, 2016, issued in U.S. Appl. No. 14/712,501.
U.S. Office Action, dated Mar. 27, 2014, issued in Application No. 14/062,717.
U.S. Office Action, dated Sep. 20, 2016, issued in U.S. Appl. No. 14/045,563.
U.S. Office Action, dated Sep. 24, 2015, issued in U.S. Appl. No. 14/749,386.
US Patent Board Decision on Appeal—Examiner Affirmed [USPTO Before the Patent Trial and Appeal Board] dated Jul. 26, 2017, issued in U.S. Appl. No. 14/029,763.
US Patent Board Decision on Appeal—Examiner Affirmed [USPTO Before the Patent Trial and Appeal Board], dated Dec. 20, 2017, issued in U.S. Appl. No. 14/045,563.
U.S. Supplemental Notice of Allowability, dated Sep. 10, 2018, issued in U.S. Appl. No. 15/427,638.
Ying et al., "Automatic Step Detection in the Accelerometer Signal," in Wearable Implant Body Sensor Networks, vol. 13, 2007, pp. 80-85.
Zichermann et al., "Gamification by Design, Implementing Game Mechanics in Web and Mobile Apps," O'Reilly Media, 2011, excerpt of pp. 55-58.

\* cited by examiner

NOTIFICATIONS ON A USER DEVICE BASED ON ACTIVITY DETECTED BY AN ACTIVITY MONITORING DEVICE

RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD

The present disclosure relates to systems and methods for presenting notifications on a user device based on user activity detected by an activity monitoring device.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness activity trackers have recently grown in popularity. Fitness activity trackers are used to measure activity, such as walking, motion, running, sleeping, being inactive, bicycling, exercising on an elliptical trainer, and the like. Typically, the data collected by such devices can be transferred and viewed on a computing device.

It is in this context that embodiments of the invention arise.

SUMMARY

Embodiments described in the present disclosure provide systems, apparatus, computer readable media, and methods for presenting notifications on a user device based on user activity detected by an activity monitoring device.

In one embodiment, a method for generating a notification on a mobile device is provided including: establishing a wireless connection to an activity monitoring device; receiving activity data from the activity monitoring device via the wireless connection; processing the activity data to determine an activity metric for a user of the activity monitoring device; comparing the activity metric against a predefined threshold, the predefined threshold being mapped to a notification message; in response to determining that the activity metric reaches or exceeds the predefined threshold, scheduling the notification message for display on the mobile device at a specified date and time; wherein the method is executed by at least one processor.

In one embodiment, the notification message defines one or more of an alert, a banner, a badge on an icon associated to the application, or a sound.

In one embodiment, establishing the wireless connection defines communication between a background executed application on the mobile device and the activity monitoring device.

In one embodiment, displaying the notification message includes triggering a local notification presenter.

In one embodiment, the notification message is displayed on the mobile device at the specified date and time.

In one embodiment, the activity metric defines one or more of a number of steps taken, a number of floors climbed, a number of calories burned, a distance traveled, or a number of active minutes.

In one embodiment, the predefined threshold defines a quantified achievement amount of an activity goal set for the user; wherein the notification message identifies the quantified achievement amount of the activity goal.

In one embodiment, the quantified achievement amount of the activity goal is less than 100%, 100%, or greater than 100% of the activity goal.

In one embodiment, the method further includes: when the specified date and time is reached, processing activity data from the activity monitoring device to identify a current state of activity of the user; and presenting or delaying presentation of the notification message, based on the identified current state of activity of the user.

In one embodiment, processing activity data to identify the current state of activity of the user includes processing location data to identify a speed or a location of the user; and presenting or delaying presentation of the notification message is based on the identified speed or location of the user.

In another embodiment, a server-executed method for presenting a notification on a mobile device is provided, including: establishing communication with the mobile device; receiving activity data from the mobile device, the activity data being processed by the mobile device from logged data received from an activity monitoring device; processing the activity data to determine an activity metric for a user of the activity monitoring device; comparing the activity metric against a predefined threshold, the predefined threshold being mapped to a notification message; in response to determining that the activity metric reaches or exceeds the predefined threshold, sending the notification message to a notification service, the notification service configured to transmit the notification message to the mobile device for rendering on the mobile device, wherein rendering the notification message includes scheduling the notification message for a time window; wherein the method is executed by at least one processor.

In one embodiment, the notification message defines one or more of an alert, a banner, a badge on an icon associated to the application, or a sound.

In one embodiment, establishing communication with the mobile device includes establishing communication with a background executed application on the mobile device.

In one embodiment, rendering the notification message on the mobile device includes triggering a notification handler.

In one embodiment, rendering the notification message occurs at the specified date and time.

In one embodiment, the activity metric defines one or more of a number of steps taken, a number of floors climbed, a number of calories burned, a distance traveled, or a number of active minutes.

In one embodiment, the predefined threshold defines a quantified achievement amount of an activity goal set for the user; wherein the notification message identifies the quantified achievement amount of the activity goal.

In one embodiment, the quantified achievement amount of the activity goal is less than 100%, 100%, or greater than 100% of the activity goal.

In one embodiment, the method further includes: when the time window is reached, processing activity data from the activity monitoring device to identify a current state of activity of the user; and presenting or delaying presentation of the notification message, based on the identified current state of activity of the user.

In one embodiment, processing activity data to identify the current state of activity of the user includes processing location data to identify a speed or a location of the user; and presenting or delaying presentation of the notification message is based on the identified speed or location of the user.

In another embodiment, a method for presenting a notification on a user device is provided including: defining an activity goal; determining a series of notification thresholds, each notification threshold defining a quantified level of achievement of an activity goal, each notification threshold being mapped to a corresponding notification message; receiving activity data measured by an activity monitoring device; processing the activity data to determine an activity metric; when the activity metric reaches one of the notification thresholds in the series of notification thresholds, triggering presentation of the corresponding notification message on a user device, wherein triggering presentation of the corresponding notification message includes scheduling the corresponding notification message for a specified date and time; wherein the method is executed by at least one processor.

In one embodiment, triggering presentation of the corresponding notification message on the user device includes activating a push notification service to transmit the notification message to the user device for rendering on the user device.

In one embodiment, triggering presentation of the corresponding notification message on the user device includes triggering a local notification presenter to display the corresponding notification message on the user device.

In one embodiment, each notification message identifies the quantified level of achievement defined by the notification threshold to which the notification message is mapped.

In one embodiment, the notification message defines one or more of an alert, a banner, a badge on an icon associated to the application, or a sound.

In one embodiment, the method further includes: rendering the notification message on the user device at the specified date and time.

In one embodiment, the activity metric defines one or more of a number of steps taken, a number of floors climbed, a number of calories burned, a distance traveled, or a number of active minutes.

In one embodiment, the method further includes: when the specified date and time is reached, processing activity data from the activity monitoring device to identify a current state of activity of the user; and presenting or delaying presentation of the notification message, based on the identified current state of activity of the user.

In another embodiment, a method for triggering a notification to a user of an activity monitoring device is provided, including: receiving activity data from one or more sensors of an activity monitoring device; processing the activity data to determine an activity metric for a user of the activity monitoring device; comparing the activity metric against a predefined threshold, the predefined threshold being mapped to a notification message; in response to determining that the activity metric reaches or exceeds the predefined threshold, establishing communication with a user device, and triggering display of the notification message on the user device, wherein triggering display of the notification message includes scheduling the notification message for display during a time window; wherein the method is executed by at least one processor.

In one embodiment, the notification message is generated in response to the determining that the activity metric reaches or exceeds the predefined threshold; and triggering display of the notification message on the user device includes sending the notification message to the user device.

In one embodiment, the method further includes: when the time window is reached, processing activity data from the one or more sensors of the activity monitoring device to identify a current state of activity of the user; and presenting or delaying presentation of the notification message, based on the identified current state of activity of the user.

In another embodiment, a server-executed method for presenting a notification on a mobile device is provided, including: establishing communication with the mobile device; receiving activity data from an activity monitoring device; processing the activity data to determine an activity metric for a user of the activity monitoring device; comparing the activity metric against a predefined threshold, the predefined threshold being mapped to a notification message; in response to determining that the activity metric reaches or exceeds the predefined threshold, sending the notification message to a notification service, the notification service configured to transmit the notification message to a mobile device for rendering on the mobile device; wherein the method is executed by at least one processor.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings.

DETAILED DESCRIPTION

Figure 1A:
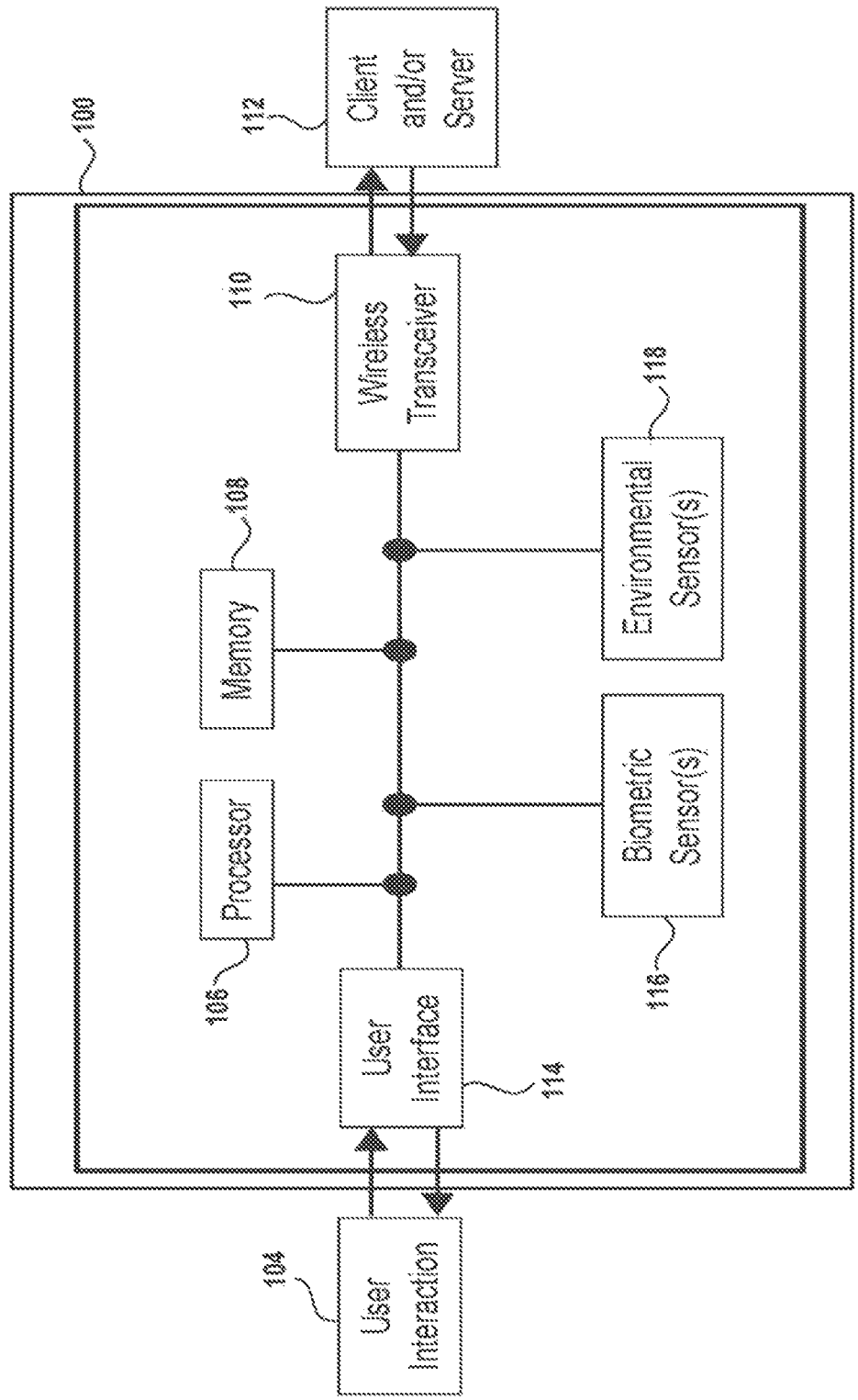
FIG. 1A shows a block diagram of an activity tracking device, in accordance with one embodiment of the present invention.

Embodiments described in the present disclosure provide systems, apparatus, computer readable media, and methods for presenting notifications on a user device based on user activity detected by an activity monitoring device.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

FIG. 1 shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. Such physical contact may be in the form of a tap or multiple taps by a finger upon the housing of the activity tracking device 100.

Figure 1B:
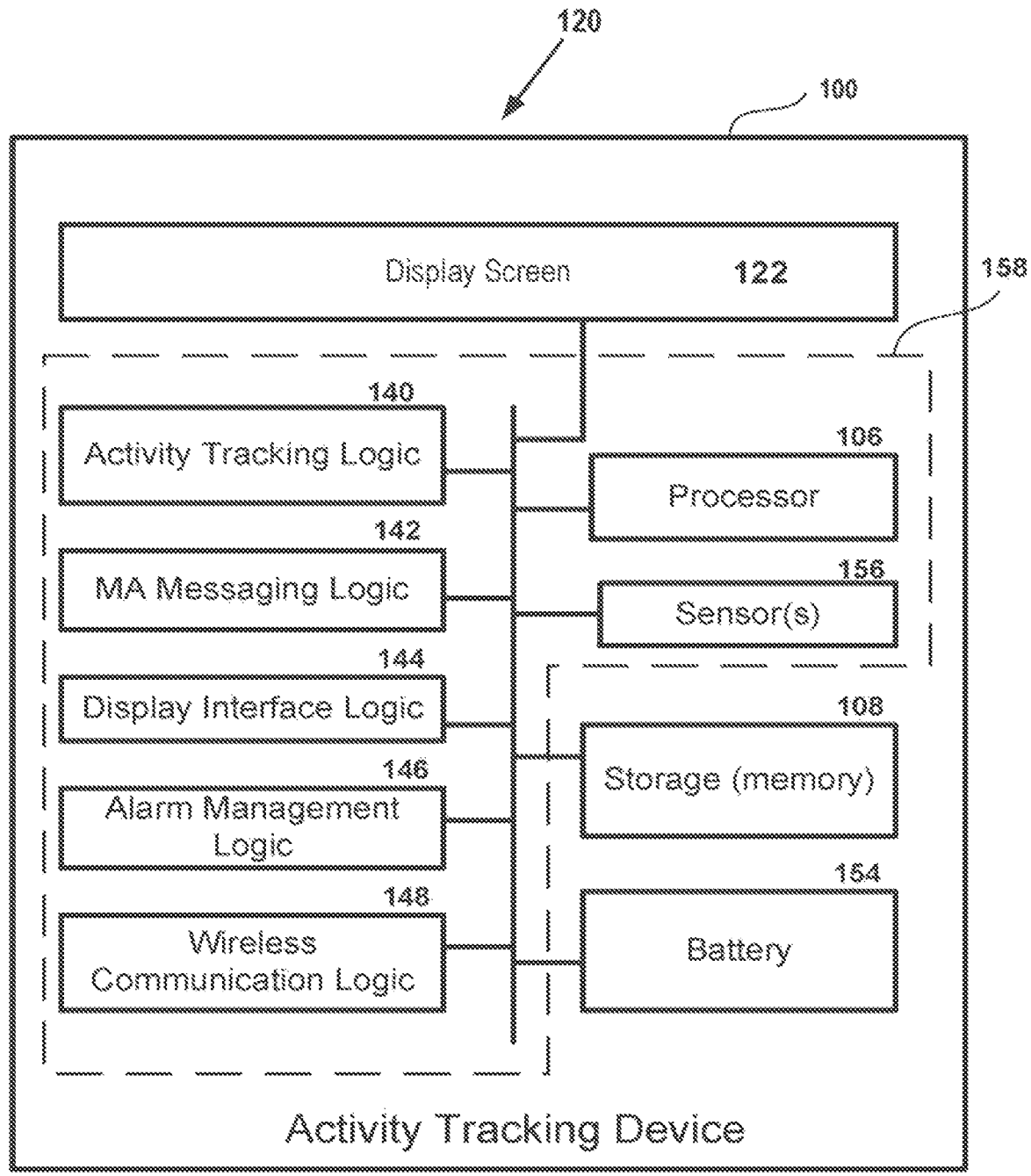
FIG. 1B illustrates an example of an activity tracking device including example components utilized for tracking activity and motion of the device, and associated interfaces to a display screen, in accordance with one embodiment of the present invention.

FIG. 1B illustrates an example of activity tracking device 100 of FIG. 1A, showing some additional example components utilized for tracking activity and motion of the device, and associated interfaces to display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 1B, the activity tracking device 100 includes logic 158. Logic 158 may include activity tracking logic 140, motion-activated messaging logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

The display interface logic 144 is configured to interface with the processor and the motion-activated messaging logic to determine when specific messages will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. It should be appreciated that the activity tracking device may communicate directly with another computing device, or indirectly via any number of intermediary devices, such as a wireless router, or other types of networking equipment (e.g. routers, switches, repeaters, etc.). The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 2:
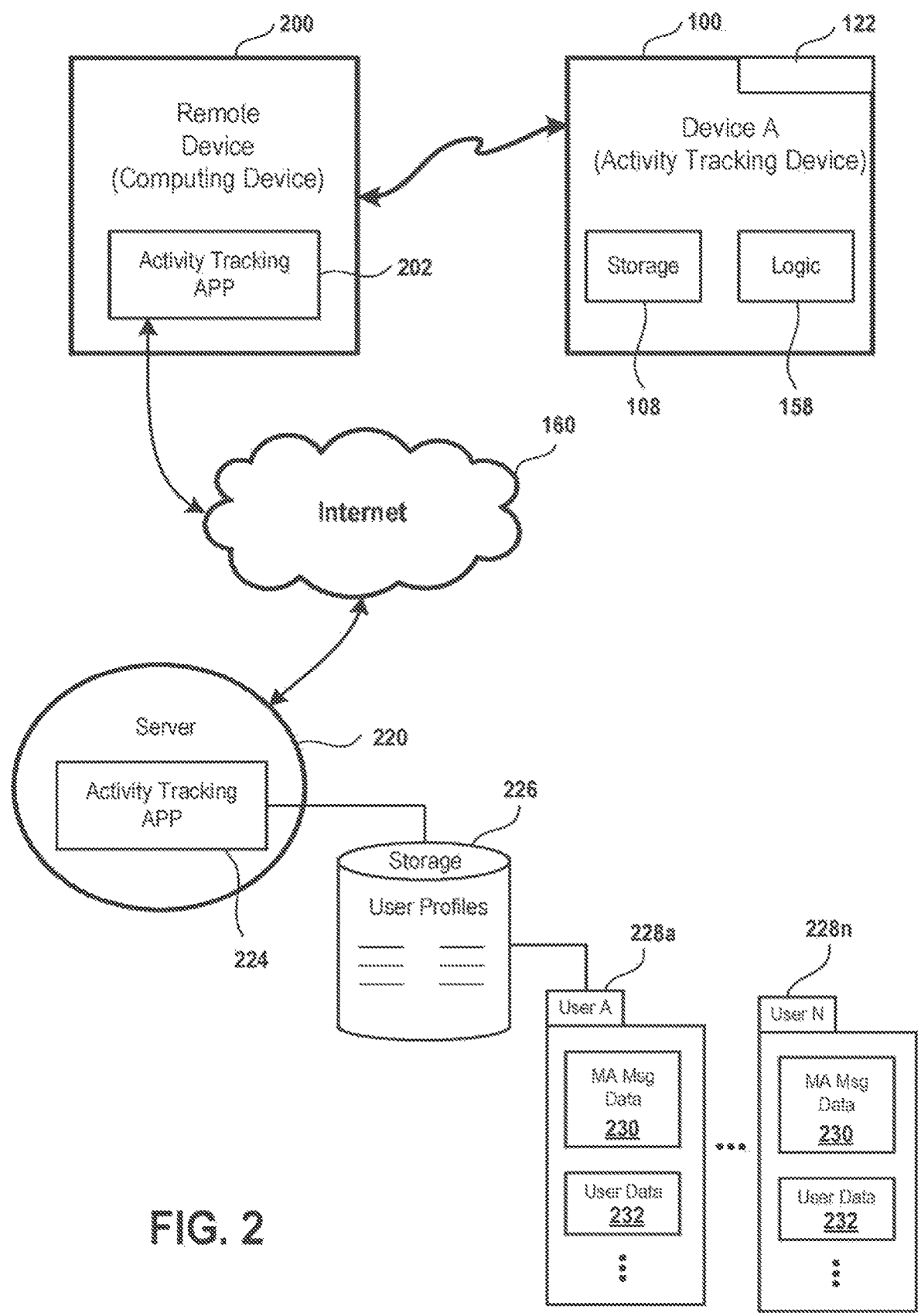
FIG. 2 illustrates an example of activity tracking device in communication with a remote device, in accordance with one embodiment of the present invention.

FIG. 2 illustrates an example of activity tracking device 100 in communication with a remote device 200. Remote device 200 is a computing device that is capable of communicating wirelessly with activity tracking device 100 and with the Internet 160. Remote device 200 can support installation and execution of applications. Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A and the Internet.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

A server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information can include, without limitation, data associated with motion-activated messaging 230, user data, etc. As will be described in greater detail below, the motion-activated messaging data 230 includes information regarding a user's preferences, settings, and configurations which are settable by the user or set by default at the server 220 when accessing a respective user account. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user. In one embodiment, the server 220 provides access to a user to view the user data 232 associated with activity tracking device.

The data viewable by the user includes the tracked motion data, which is processed to identify a plurality of metrics associated with the motion data. The metrics are shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

Figure 3:
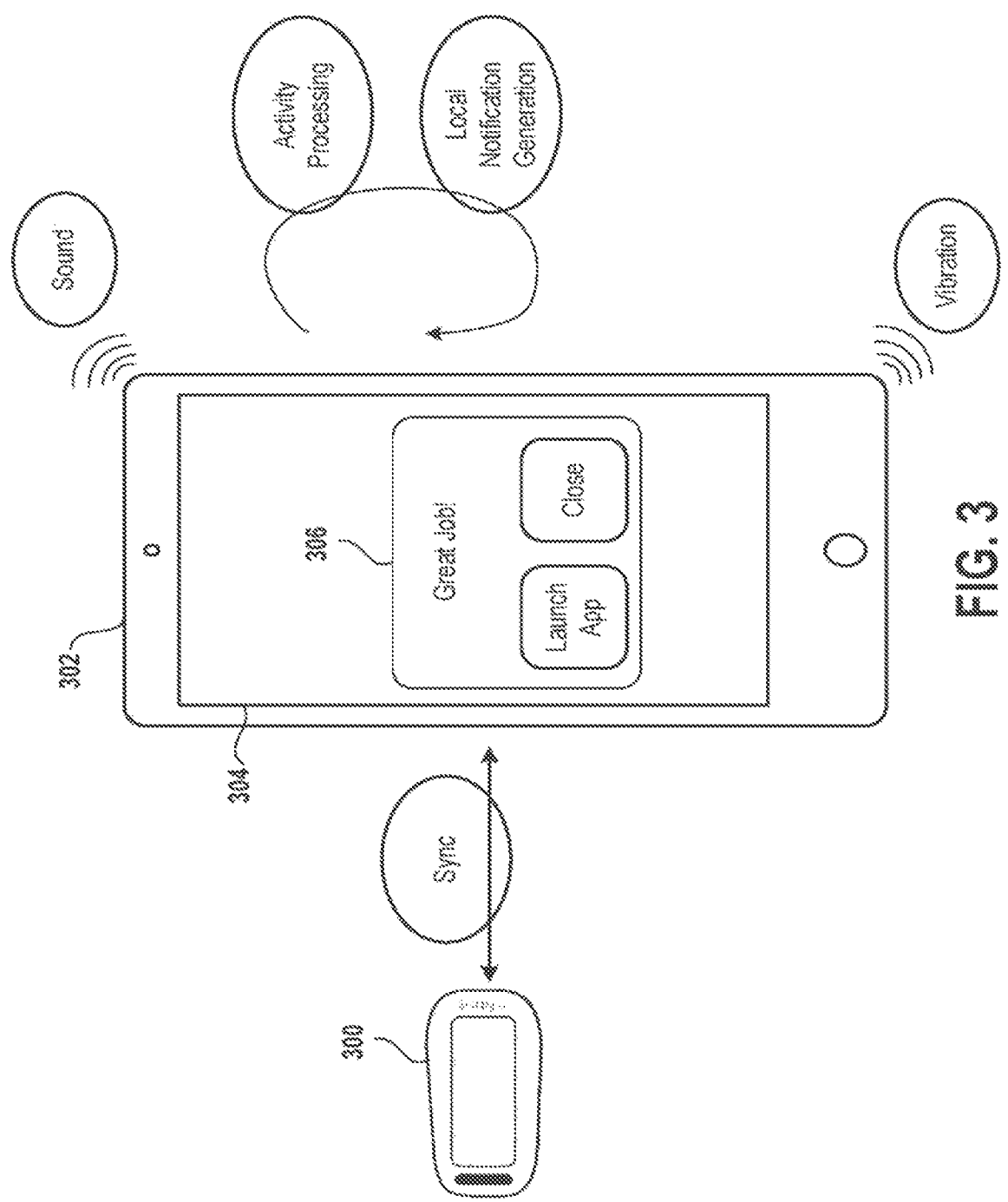
FIG. 3 illustrates a system for presenting a locally generated notification, in accordance with an embodiment of the invention.

FIG. 3 illustrates a system for presenting a locally generated notification, in accordance with an embodiment of the invention. In the illustrated embodiment, an activity monitoring device 300 is configured to record activity data based on output from various sensors included in the activity monitoring device 300. The activity data may include raw sensor data and/or data identifying specific user activity processed from the raw sensor data, such as individual steps taken over time, changes in distance over time, altitude changes over time, etc. The activity data recorded by the activity monitoring device 300 may be further processed at the activity monitoring device 300 to determine various activity metrics which quantify the activity data, such as determining the number of steps taken, distance traveled, steps/floors climbed, calories burned, active minutes, etc.

During a synchronization operation with a user device 302, the activity monitoring device 300 uploads the activity data and/or activity metrics to the user device 302. The user device 302 can be any computing device, including, without limitation, a mobile device, cellular phone, tablet computer, personal computer, laptop computer, or any other computing device that may be configured to present notifications in accordance with embodiments described herein. It will be appreciated that during the synchronization operation, previously collected activity data and/or activity metrics can be uploaded to the user device 302. In addition, synchronization may entail ongoing updates from the activity monitoring device 300 to the user device 302. That is, as new activity data or metrics are generated at the activity monitoring device 300, they can be uploaded to the user device 302 in a continuing fashion. This continual uploading may occur with various frequency depending upon the desired level of time synchronization between generation of activity data at the activity monitoring device and receipt by the user device. In one embodiment, updates may occur with sufficient frequency to be substantially real-time or near real-time. In other embodiments, updates may occur with less frequency. In one embodiment, updates occur when new activity data/metrics are available. In various embodiments, updates occur when a threshold amount of new activity data is accumulated, or when a threshold change in activity data/metrics occurs, or when specific types of activity data are generated, etc. Additionally, it will be appreciated that in various embodiments, various combinations of techniques can be employed to provide ongoing continual updates from the activity monitoring device 300 to the user device 302.

At the user device 302, the activity data/metrics can be processed to determine whether a notification should be provided to the user on the user device 302. If a notification is triggered, then a local notification generation process occurs, and a notification is provided to the user at the user device 308. In one embodiment, the notification defines a display of a notification message 306 on a display 304 of the user device 302. In the illustrated embodiment, the notification message 306 is configured to congratulate the user, and the display of the notification message 306 further includes buttons which allow the user to close the message, or launch an application on the user device 302 for interfacing with the activity monitoring device 300. In other embodiments, additional methods for notifying the user can be activated, such as a flashing light or a sound or a vibration/haptic feedback at the user device 302.

A notification can be triggered based on the activity data/metrics in a number of ways, and the specific embodiments described herein are provided by way of example, and not by way of limitation. For example, in some embodiments, a notification is presented when a threshold for a particular activity metric is reached. By way of example, a notification may be presented when one of the following thresholds is reached: a threshold number of steps taken, a threshold number of steps/floors (or altitude) climbed, a threshold distance traveled, a threshold number of active minutes achieved, a threshold number of calories burned, etc.

Thresholds may define goals for the user to attain. Such goals can be generic or otherwise system-defined goals, such as specific milestones denoting various achievement levels. Thresholds may also be user-defined, indicating personal goals of a particular user. Notifications which are triggered by reaching such thresholds can thus be indicative of achievements by the user, and serve to congratulate or encourage the user in their fitness activity.

Furthermore, in some embodiments, notification thresholds can be defined as a portion (ranging from less than 100% to greater than 100%) of a specific milestone or goal. It may be useful to inform the user of their progress toward a particular goal, and therefore, notification thresholds can be configured to update the user as they progress towards the goal. For example, notification thresholds may be defined at regular subdivisions of the goal, such as at 25%, 50%, 75%, and 100% of the goal. In other words, notification thresholds may be defined at the following: 1/n, 2/n, 3/n, etc., where n is the number of portions into which the goal metric amount is subdivided. It will be appreciated that at each of these thresholds, a corresponding notification message can be triggered to be presented on the user device, perhaps indicative of the activity metric amount relative to the goal that has been achieved, or the activity metric amount remaining to achieve the goal. Of course, in various embodiments, some or all of such thresholds may be utilized, and such may depend upon user-defined settings defining the notification thresholds which will trigger notifications presented to a specific user. For example, the user may indicate that they wish to receive notifications each time they reach another 20% of their goal, or that they only wish to receive a notification when they are within 20% of achieving their goal (i.e. have reached 80% of their goal) or when they have achieved their goal, etc.

Additionally, it will be appreciated that notification thresholds may be set for a predefined quantity of a given activity metric that is remaining to achieve a particular goal. For example, a notification threshold may be set for when a user is within x number of steps (or stairs/floors climbed, distance traveled, calories burned, active minutes, etc.) of reaching their goal. Furthermore, notifications may be triggered when the user reaches a predefined amount exceeding a particular goal, such as a specific fraction or percentage exceeding the goal, or a predefined number amount of a specific activity metric exceeding the goal. A notification message triggered by such an event may congratulate the user on exceeding the goal or milestone (e.g. congratulate the user on being an "overachiever").

In the presently described embodiments, it is broadly contemplated that activity data and metrics are detected at the activity monitoring device, whereas the processing of such data to trigger display of a notification is performed at the user device on which the notification is displayed. It should be appreciated that this is merely one example of a division of processing operations between the activity monitoring device and the user device, in order to produce display of a notification on the user device. In other embodiments, the various processing operations which are required to effect display of a notification on the user device can be divided between the activity monitoring device and the user device in any possible configuration. For example, in one embodiment, the processing of the activity data as well as the triggering of the notification are performed at the activity monitoring device, and upon triggering of the notification, the notification message is sent to the user device for display on the user device (e.g. a smart watch).

Figure 4:
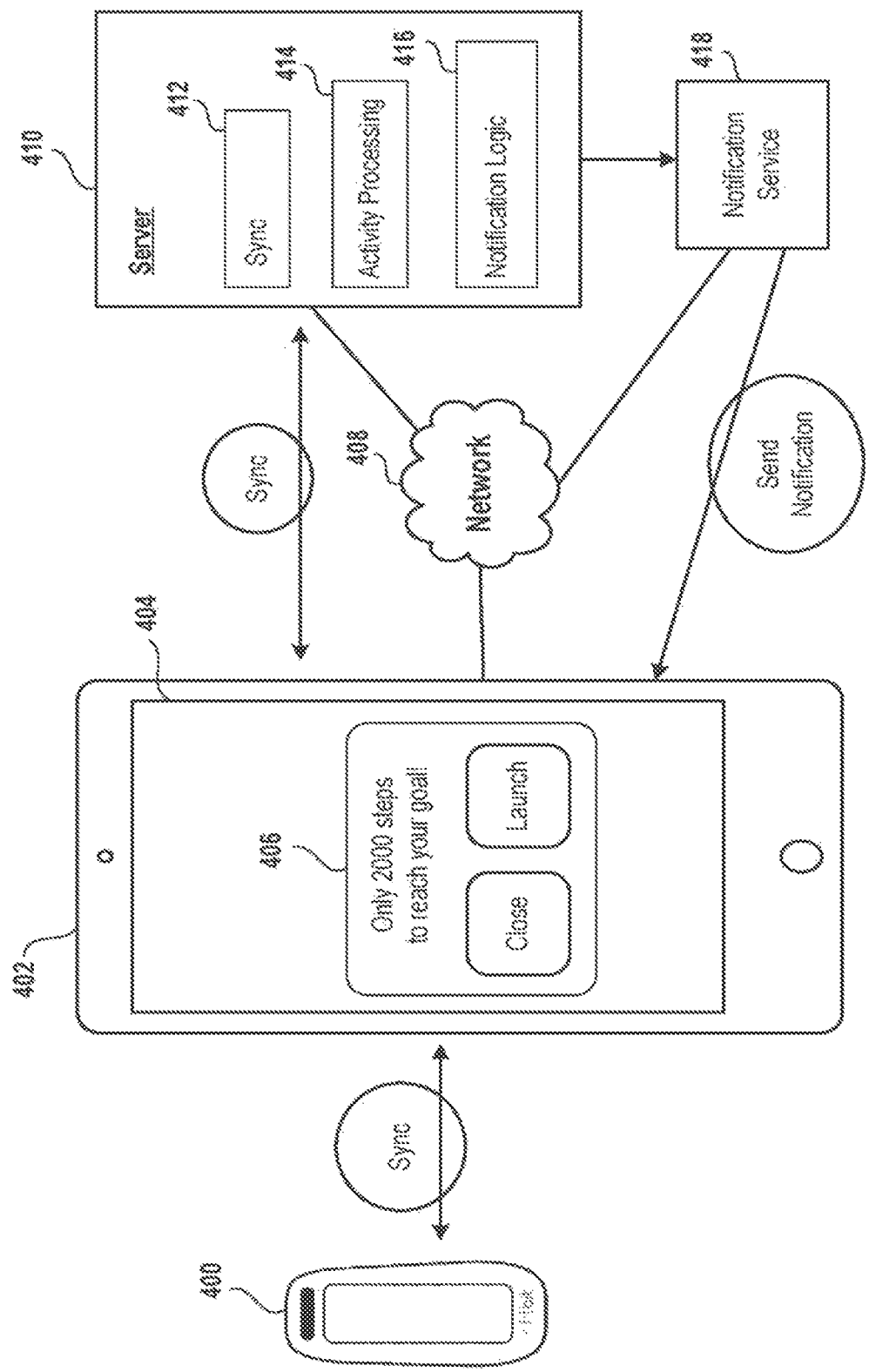
FIG. 4 illustrates a system for triggering notifications on a user device based on activity detected by an activity monitoring device, in accordance with an embodiment of the invention.

FIG. 4 illustrates a system for triggering notifications on a user device based on activity detected by an activity monitoring device, in accordance with an embodiment of the invention. The illustrated embodiment is conceptually similar to that shown and described with reference to FIG. 3; however, in the embodiment of FIG. 4, the notification is triggered at a remote server, which in turn is configured to push a notification to the user device. As shown, an activity monitoring device 400 is configured to upload activity data/metrics to a user device 402 during a synchronization process, which can be a foreground or background synchronization process. The user device 402 in turn is configured to upload the activity data/metrics to a remote server 410 as part of the synchronization process. Additionally, it is noted that the user device 402 may process the activity data/metrics received form the activity monitoring device 400 to generate additional activity data/metrics prior to uploading to the server 410.

The server 410 is configured to include a synchronization module 412 for handling the server-side processing of the synchronization procedure, including receiving and storing the activity data/metrics received from the user device 402. An activity processing module 414 is configured to process or analyze the activity data/metrics to determine whether a notification should be triggered. If it is determined that a notification should be triggered, then notification logic 416 is activated to generate the notification. The generation of the notification may include retrieving a notification message that corresponds to a given notification threshold, and communicating the notification message to a notification service 418 and instructing or requesting the notification service 418 to "push" the notification to the user device 402. A "push" notification will be understood by those skilled in the art to define a notification that is sent to and rendered on a client device (e.g. user device 402 in the illustrated embodiment) by a remote system/server. A push notification is initiated by the remote system (e.g. notification service 418), though the resulting notification is presented on the client device (e.g. user device 402). One example of a push notification service is the Apple Push Notification Service.

In the illustrated embodiment, a notification message 406 is presented on the display 404 of the user device 402. By way of example, the notification message 406 indicates that the user needs 2000 more steps to reach their goal. Option buttons are presented to either close the notification, or launch an application that can interface with the activity monitoring device 4000.

Figure 5:
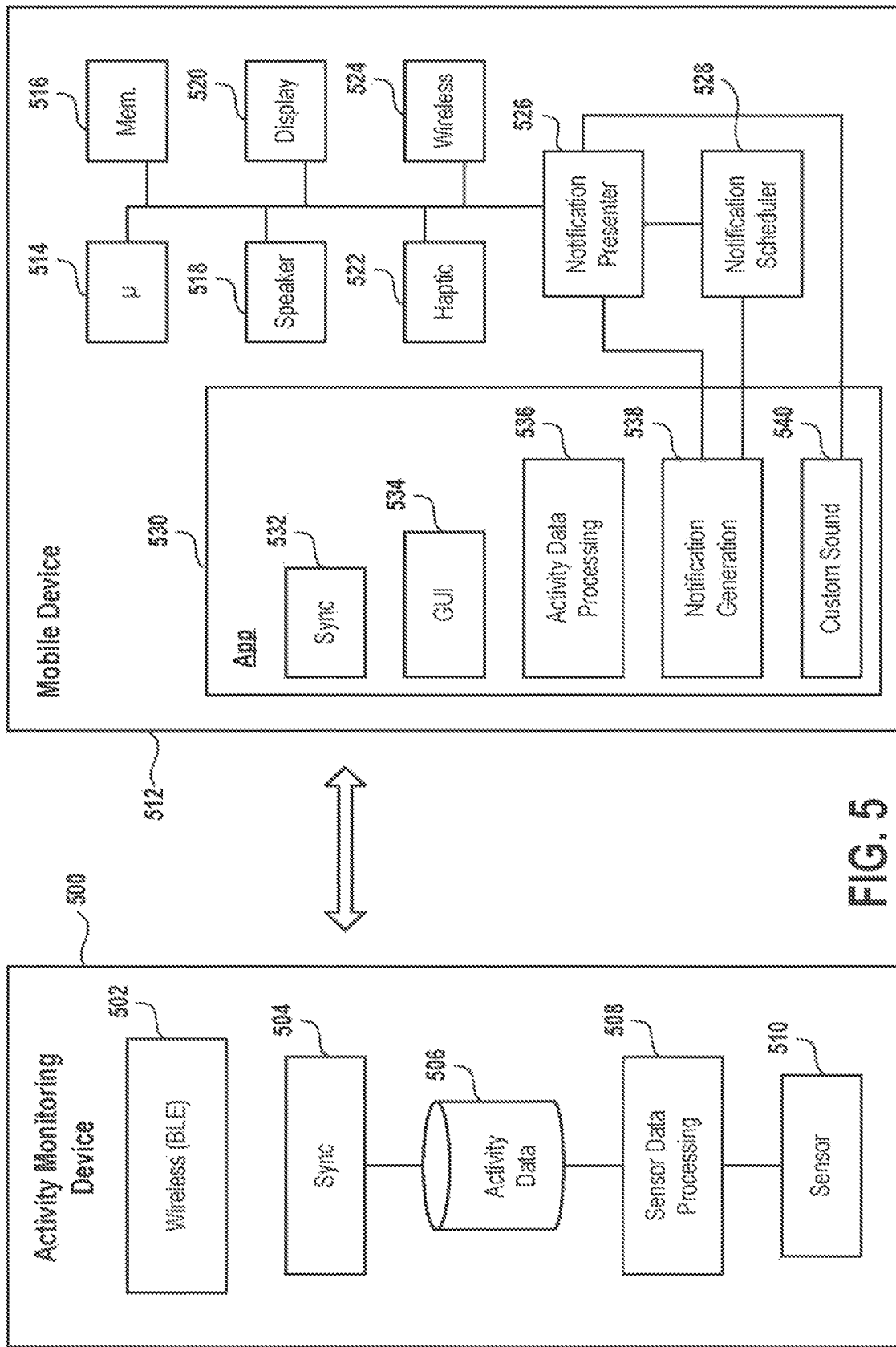
FIG. 5 illustrates components of a system for presenting a notification on a mobile device, in accordance with an embodiment of the invention.

FIG. 5 illustrates components of a system for presenting a notification on a mobile device, in accordance with an embodiment of the invention. An activity monitoring device 500 is provided for tracking activity of a user. In the illustrated embodiment, the activity monitoring device 500 includes a wireless module 502 for handling wireless communication with the mobile device 512. A sync module 504 is configured to handle data synchronization operations, including uploading activity data/metrics from an activity data storage 506 to the mobile device 512. One or more sensors 510 can include any of various environmental or biometric sensors. A sensor data processing module 508 is configured to process data generated by the sensors 510.

The mobile device 512 includes a processor 514 and a memory 516 for executing and storing program instructions, respectively. A speaker 518 is provided for reproducing predefined sounds. A display 520 is provided for visually rendering information. A haptic feedback module 522 is configured to provide tactile feedback, such as vibration of the mobile device 512. A wireless module 524 is configured to handle wireless communication of the mobile device, including wireless communication with the activity monitoring device 500. In one embodiment, the wireless communication between the activity monitoring device 500 and the mobile device 512 is a Bluetooth low energy connection.

A notification presenter 526 is configured to present notifications on the mobile device. The notification presenter 526 receives requests from applications (e.g. application 530) to present a notification on the mobile device 512. The requests may define content of the notification, such as a message, sound, haptic feedback, whether an option to launch the application (in the foreground) from which the notification request was generated, etc. In response to receiving a notification request, the notification presenter 526 is configured to activate the relevant modules of the mobile device 512 to present the notification to the user. For example, a message may be displayed on the display 520, or a sound may be played through the speaker 518, or haptic sensations may be provided via the haptic module 522.

The application 530 includes a sync module 532 for handling synchronization operations with the activity monitoring device 500, including receiving activity data/metrics from the activity monitoring device 500. This may occur over the aforementioned wireless connection via the wireless module 524. The application 530 may define a graphical user interface 534 configured to enable the user to comprehend data from the activity monitoring device 500, as well as manage the device. An activity data processing module 536 is configured to process and analyze activity data/metrics received from the activity monitoring device 500. This may entail generation of and/or updating of activity metrics.

A notification generator 538 is configured to determine when to trigger a notification based on activity data/metrics of the user. As has been discussed, various thresholds may be defined based on various activity metric goals. The notification generator 538 can thus be configured to compare a particular activity metric against one or more predefined threshold values to determine whether or not to trigger a notification to the user. When a given predefined threshold value is reached, then the notification generator 538 is configured to retrieve and associated notification message and generate a notification to the user. If the notification is to be presented immediately, then the notification presenter 526 is activated. The notification generator 538 communicates the relevant parameters of the notification, including the notification message content and any other optionally define parameters, to the notification presenter 526, which is then configured to execute the rendering of the notification, such as by displaying the notification message on the display 520 of the device 512.

The notification generator 538 may also be configured to determine whether the present time is an appropriate time to provide a notification to the user. For example, it may not be desirable to provide a notification to the user during hours of the day when the user is likely to be asleep, or when it can be determined that the user is otherwise unlikely to be able to view or comprehend notification. In such instances, it can be useful to schedule notification for a later time. Therefore, the notification generator 538 can be configured to activate a notification scheduler 528, which receives the relevant information defining the notification, and schedules the rendering of the notification on the mobile device 512 for a later time. In another embodiment, the notification scheduler 528 can be configured to schedule the notification for rendering during a specified time window or period of time. In another embodiment, the notification scheduler 528 functions as a configurable timer that then triggers the notification generator 538 to activate the notification presenter 526 in order to render the notification to the user. It should be appreciated that though notifications can be scheduled for rendering, the actual rendering of the scheduled notification can be subject to other considerations (e.g. current state of activity detected via the activity monitoring device, or other considerations described herein for determining whether to render a notification).

It will be appreciated that there can be many instances when the user is unlikely to be able to view or comprehend the notification, or when it is otherwise undesirable to provide a notification to the user, even though a notification threshold has been reached. For example, data obtained from a calendar associated with the user may indicate that the user is busy or occupied during a specific time period, and therefore it is not desirable to notify the user during the specific time period. It might also be determined that the user is currently engaged in physical activity based on data received from the activity monitoring device, and that the user is therefore unavailable to receive a notification.

In one embodiment, real-time data received from the activity monitoring device is analyzed to determine a current state of activity of the user, and based on the determined state of activity, a notification can be rendered to the user in immediate response to reaching a particular activity metric threshold, or may be delayed. However, in other embodiments, the current state of activity can be utilized to determine whether to present, or delay the presentation of, the notification message. The state of activity of the user can identify particular physical activity states, such as running, walking, swimming, biking, etc. which may be applied to determine when to present a notification message. For example, a user might reach a milestone during the course of a run, and so a notification message is prepared for the user. However, the presentation of the notification message can be delayed until it is determined that the user has slowed to a walk or otherwise stopped running. In this manner, the notification is presented to the user during a time when the user is more likely to be able or willing to view it.

In some embodiments, location data (e.g., GPS data) can be utilized to determine when to present a notification message. For example, location data can be analyzed to determine the current speed or location of the user, and a notification message may be presented or delayed based on the speed or location of the user. In one embodiment, a notification message may be presented when the current speed is determined to be below a predefined threshold speed. Otherwise, when the current speed reaches or exceeds the predefined threshold speed, the presentation of the notification message is delayed until it falls below the predefined threshold speed. In another embodiment, variance in the speed of the user can be utilized to determine when to present a notification message. For example, in one embodiment, a notification message is presented if the speed of the user varies by less than a predefined amount; whereas the notification message is not presented if the variance of the speed of the user reaches or exceed the predefined amount.

In another embodiment, location data can be analyzed to determine the user's location with respect to geographical features, and the presentation of notification messages can be determined based on such information. For example, a notification message might be presented when it is determined that the user has reached the end of a trail, or climbed to the top of a hill, etc. In another example, a notification message might be delayed until it is determined that the user has returned to a particular geographic location, such as their home or their starting point (e.g., a parking lot, trailhead, etc.).

In one embodiment, when it is determined that the user is currently engaged in physical activity having an intensity level above a certain threshold, then the rendering of the notification is delayed until the intensity level of the physical activity is reduced to the threshold. In another embodiment, if it is determined based on real-time data received from the activity monitoring device that the user is currently sleeping, then the notification is delayed until it is determined that the user is currently awake. The foregoing examples of activity based delay of a notification are provided merely by way of example, without limitation. In various embodiments, it will be appreciated that activity of a user as determined from real-time data received from the activity monitoring device can be analyzed in a variety of ways to determine when it is appropriate to render a notification to the user, and thereby delay or schedule or present a notification accordingly.

Figure 6:
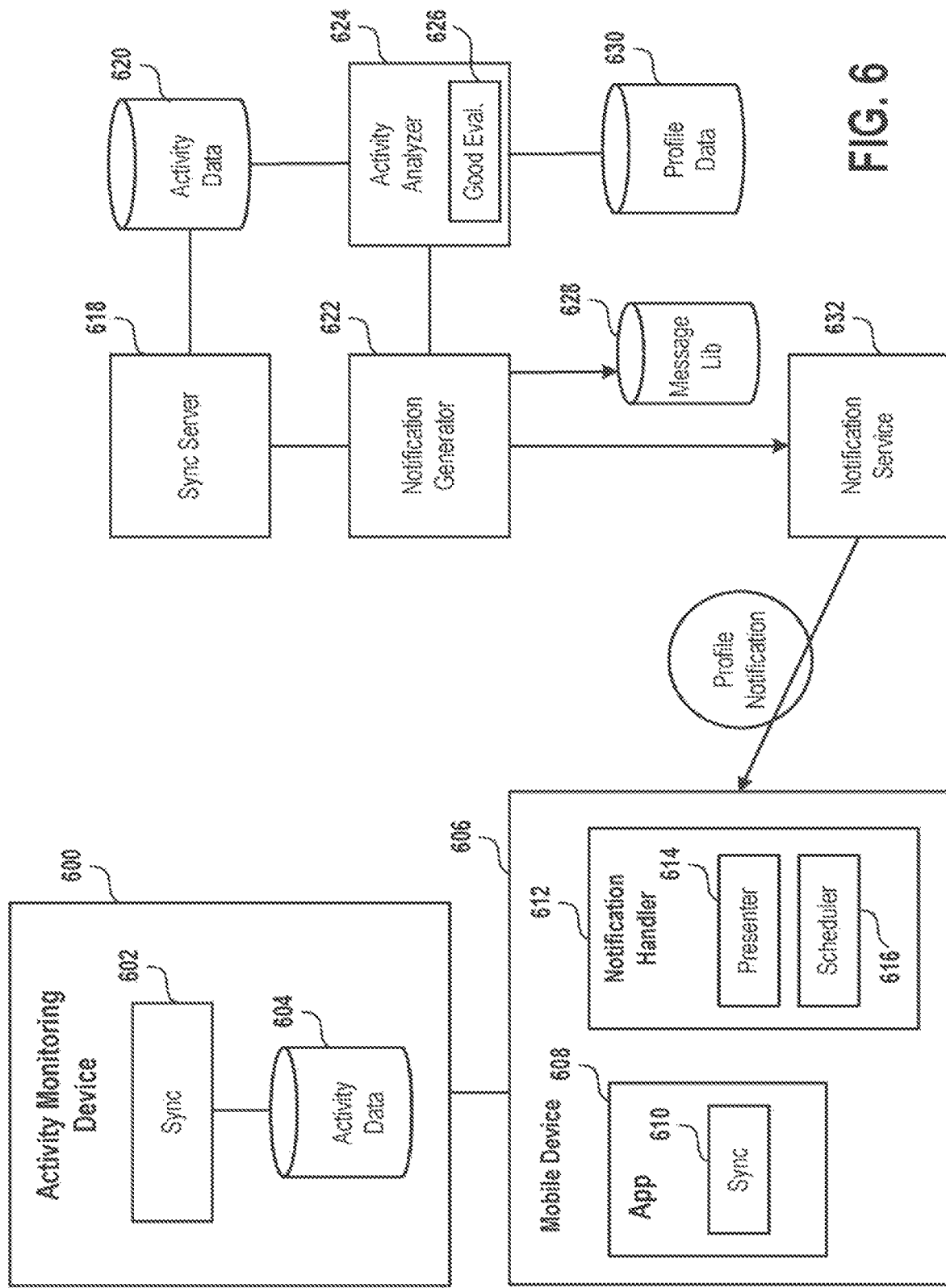
FIG. 6 illustrates a system for rendering a notification to a user based on tracked activity of the user, in accordance with an embodiment of the invention.

FIG. 6 illustrates a system for rendering a notification to a user based on tracked activity of the user, in accordance with an embodiment of the invention. An activity monitoring device 600 is configured to detect and record activity of the user, and includes activity data storage 604 for storing such detected activity of the user. A synchronization module 602 is configured to handle synchronization operations with a mobile device 606, including uploading of activity data/metrics to the mobile device 606.

The mobile device 606 includes an application 608 that is configured to interface with the activity monitoring device 600. The application 608 includes a synchronization module 610 that is configured to handle synchronization operations at a mobile device 606, which may include receiving activity data/metrics from the activity monitoring device 600, as well as uploading activity data/metrics to a synchronization server 618. It will be appreciated that activity data and/or metrics can be processed to various extents by each of the activity monitoring device 600 and the mobile device 606.

The synchronization server 618 is configured to receive and store the activity data/metrics from the mobile device 606 into an activity data storage 620. An activity analyzer 624 is configured to access profile data associated with the user of the activity monitoring device from a profile data storage 630. This profile data can define one or more activity metric goals for the user. In addition, the profile data may define various notification thresholds in relation to a specific activity metric goal, as has been discussed above. By way of example, one threshold may be defined for when a user's activity metric approaches to within a certain amount of the activity metric goal, another defined by the activity metric goal itself, and another defined when the user exceeds the activity metric goal by a certain amount. Each of these thresholds can be associated with a particular notification message that is stored in a message library 628.

The activity analyzer 624 includes a threshold evaluation module 626 that is configured to determine when the relevant activity metric of the user reaches a predefined threshold, and thereupon trigger a notification generator 622 to retrieve the notification message associated with the predefined threshold from the message library 628, and activate a notification service 632 to send a push notification request to the mobile device 606. In one embodiment, the notification generator 622 accesses an API of notification service 632, providing a request to the notification service 632 with relevant parameters including the contents of the notification message and identification of the specific mobile device 606 to which the push notification is to be sent.

Mobile device 606 includes a notification handler 612 that is configured to manage notification requests. In the illustrated embodiment, the notification handler 612 of the mobile device 606 receives a push notification requests from the notification service 632, and, and activates a notification presenter 614 that is configured to render the push notification on the mobile device 606. Alternatively, the notification handler 612 also includes a notification scheduler 616 that is configured to schedule the push notification for rendering at a later time.

Though systems for presenting a notification to a user have been described with reference to presentation of the notification on a mobile device, it will be appreciated by those skilled in the art that notifications in accordance with various embodiments of the invention can be rendered on any other type of computing device that is configured for rendering such notifications. It will be understood that a notification may be presented to a user in different formats depending upon the context in which the notification is rendered. For example, during an active session of the computing device, the notification may be rendered as a pop up message or window within the contextual operating environment on the computing device, and clicking on an appropriate location may cause it to disappear, or may activate the activity tracking application for viewing information that is related to the notification.

In a mobile device operating environment, a notification presentation may depend upon whether its associated application is presently running in the foreground. If so, then the notification information (or payload) may be passed directly to the foreground application and is handled by the application based on the application's configuration. Whereas, if the application is not running or is only running in the background, then the notification is rendered (or scheduled to be rendered) on the mobile device with an option to "view" or otherwise launch the application into the foreground. Selection of this option may cause the notification payload to be passed to the application, as the application is launched into the foreground.

Figure 7:
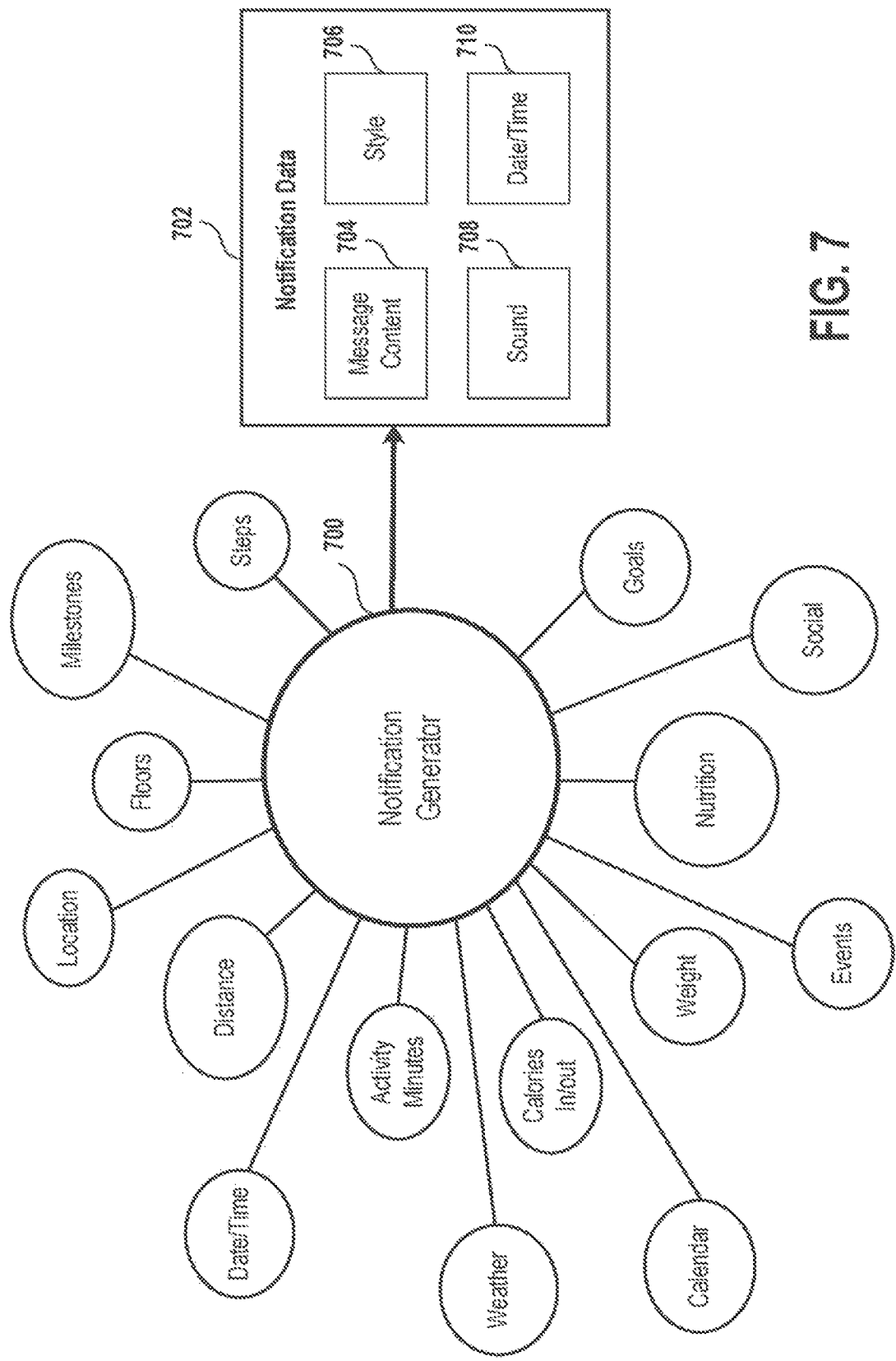
FIG. 7 illustrates a variety factors which may be considered for purposes of triggering a notification, in accordance with embodiments of the invention.

In various embodiments, it will be appreciated that notifications in accordance with embodiments of the invention can be generated based a number of factors, alone or in combination. FIG. 7 illustrates a variety factors which may be considered for purposes of triggering a notification, in accordance with embodiments of the invention. Furthermore, the content of a resulting notification can include or be based upon data defined by such factors. In the illustrated embodiment, a notification engine 700 is configured to evaluate the various factors and generate a notification based on such factors when it is determined that a notification should be provided to the user. Broadly speaking, notification data may be generated to define a given notification, including such information items as the following: message content 704 which defines text for a notification; a style 706 designating a particular style for the notification, such as a pop-up message, a badged icon, or other selectable notification style; a sound 708 defining or identifying audio to be rendered in accordance with the notification; a date/time 710 at which the notification is to be rendered.

As has been discussed, specific goals and/or milestones can be utilized to define thresholds for activity metrics of a user which will trigger generation of notifications. In addition to these threshold-based triggers, notifications can be defined in relation to user activity in other ways. For example, the notification generator 700 can be configured to generate notifications at regular intervals (e.g. daily, weekly, etc.) which update the user about one or more activity metrics, or their progress toward a goal/milestone, etc. The content of such notifications might include a current amount of a particular activity metric or an amount remaining to achieve a particular goal or milestone.

In another embodiment, notifications can be generated based on a detected change in activity data/metrics, such as an increase or decrease in the activity data/metric by a certain amount. The detected change may also be considered relative to the amount of time over which the change occurs. For example, a change of a particular amount occurring within a particular timespan may trigger a notification (e.g. user runs a mile in eight minutes, burns 500 calories in an hour, climbs ten floors in three minutes, etc.). In another embodiment, a change relative to an earlier time period may trigger a notification (e.g. increasing/decreasing the number of steps taken in a week over that taken during the previous week). In other embodiments, personal best accomplishments for a given user may trigger notifications (e.g. walking the most steps, or burning the most calories, or climbing the most stairs/floors, or traveling the greatest distance, over a given timespan such as a single day). In another embodiment, achieving a particular rate of change in an activity metric may trigger a notification (e.g. running at or above a particular speed, climbing at or above a particular rate of altitude gain, exercising at or above a particular calorie burning rate, etc.). It will be appreciated that in the foregoing embodiments relating to notifications generated in response to detected changes in activity data/metrics, the content of such notifications can include or be based upon the data which defines the change in the activity data/metrics. Such notifications may also include congratulatory messages, an option to share to a social network, etc.

It will be appreciated that notifications can be triggered and generated based on any number of activity metrics, including a number of steps taken, number of floors/stairs climbed, distance traveled, number of active minutes, calories burned, etc. Notifications may also be triggered or generated based on additional fitness related information, such as an indicated or calculated weight of the user, nutrition information provided by or otherwise associated with the user, etc. Additionally, notifications can be generated based on numerous other factors, some of which are described herein by way of example, without limitation.

In one embodiment, the notification may be generated based on an identified location of the user. For example, the notification might be triggered by a change in location of the user, such as detection that the user has moved to a different city, state, or country. The content of a notification can be configured to be location sensitive, for example, utilizing the appropriate language of the identified location of the user, which may also include the usage of local terminology or slang.

In one embodiment, a notification can be generated based on a current date or time. For example, a notification occurring during the morning hours of the day may include the phrase "good morning." As another example, on the date of a holiday, the contents of a notification can be configured to reference the holiday or otherwise be appropriate to the holiday (e.g. "Happy Halloween"). A similar concept can be extended to encompass multiple days or seasons, wherein notification messages during such time include content that is thematically appropriate to the season (e.g. "Happy holidays!").

In one embodiment, a notification can be generated based on the current or forecasted weather, which may be determined in accordance with an identified location of the user. For example, if the weather is determined to be cold, then a notification may encourage the user to dress warmly, whereas if the weather is determined to be hot, then a notification may encourage the user to stay hydrated. It will be appreciated that a great variety of weather appropriate messages can be generated as notifications to the user.

In one embodiment, a notification can be generated based on a calendar associated with a given user. For example, the timing of notifications can be determined in part based on the user's calendar, such as by avoiding sending notifications to the user during times when it is indicated on the calendar that the user is busy or occupied. A notification might reference a specific event listed on the user's calendar, such as in the case of a reminder notification which reminds the user about an upcoming event, or a post-event notification occurring after the expiration of an event on the user's calendar. A post-event notification might encourage a user to log details about the event, share to a social network, etc.

In a related embodiment, a notification can be generated based on local or community events occurring in the geographic vicinity of the user. A notification might inform a user about an upcoming event (e.g. a local charity run), or if it is known that a user has participated in such an event, then the notification might encourage the user to log details about the event, rate the event, share about the event to the social network, etc.

In one embodiment, a notification can be generated based on social network activity associated with the user, such as posts generated by friends/members of a social graph of the user.

Figure 8:
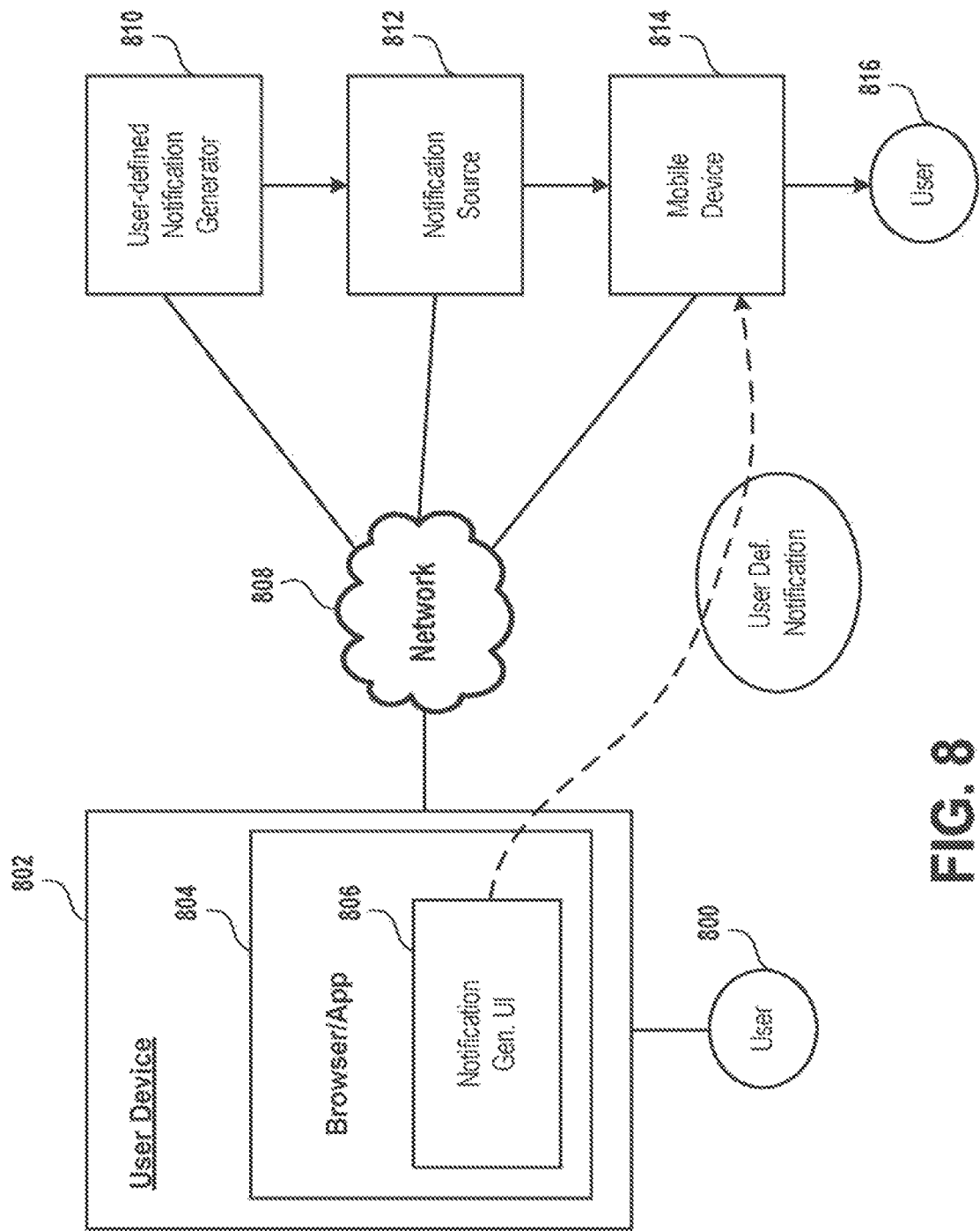
FIG. 8 illustrates a system for enabling a first user to define a notification for presentation to a second user, in accordance with an embodiment of the invention.

FIG. 8 illustrates a system for enabling a first user to define a notification for presentation to a second user, in accordance with an embodiment of the invention. In the illustrated embodiment, the first user 800 interacts with a user device 802. The first user 800 accesses a notification generation user interface 806, which may be included as part of an application or accessed via a browser as indicated by reference 804. Broadly speaking, the notification generation user interface 806 provides tools for the user 800 to define the contents and other options for a notification to be presented to a second user 816. By way of example, the user interface 806 may provide a text entry interface for the user 800 to enter text to be included in the notification, a user selection interface for the user 800 to identify the user to whom the notification will be sent, as well as other options which may define various aspects of the notification.

These definitional aspects of the notification as specified by the user 800 are communicated over the network 808 to a user-defined notification generator 810. The user-defined notification generator 810 is configured to send a request to a notification service 812 to generate a notification to the second user 816 based on the parameters provided by the first user 800. The notification service 812 in turn generates a push notification to a corresponding mobile device 814 that is associated with the user 816. Though a push notification to a mobile device is generally contemplated in accordance with embodiments of the invention, it will be appreciated that in other embodiments other types of devices accommodating other types of notification schemas can be employed to allow a notification having parameters defined by a first user to be sent to a second user.

Figure 9:
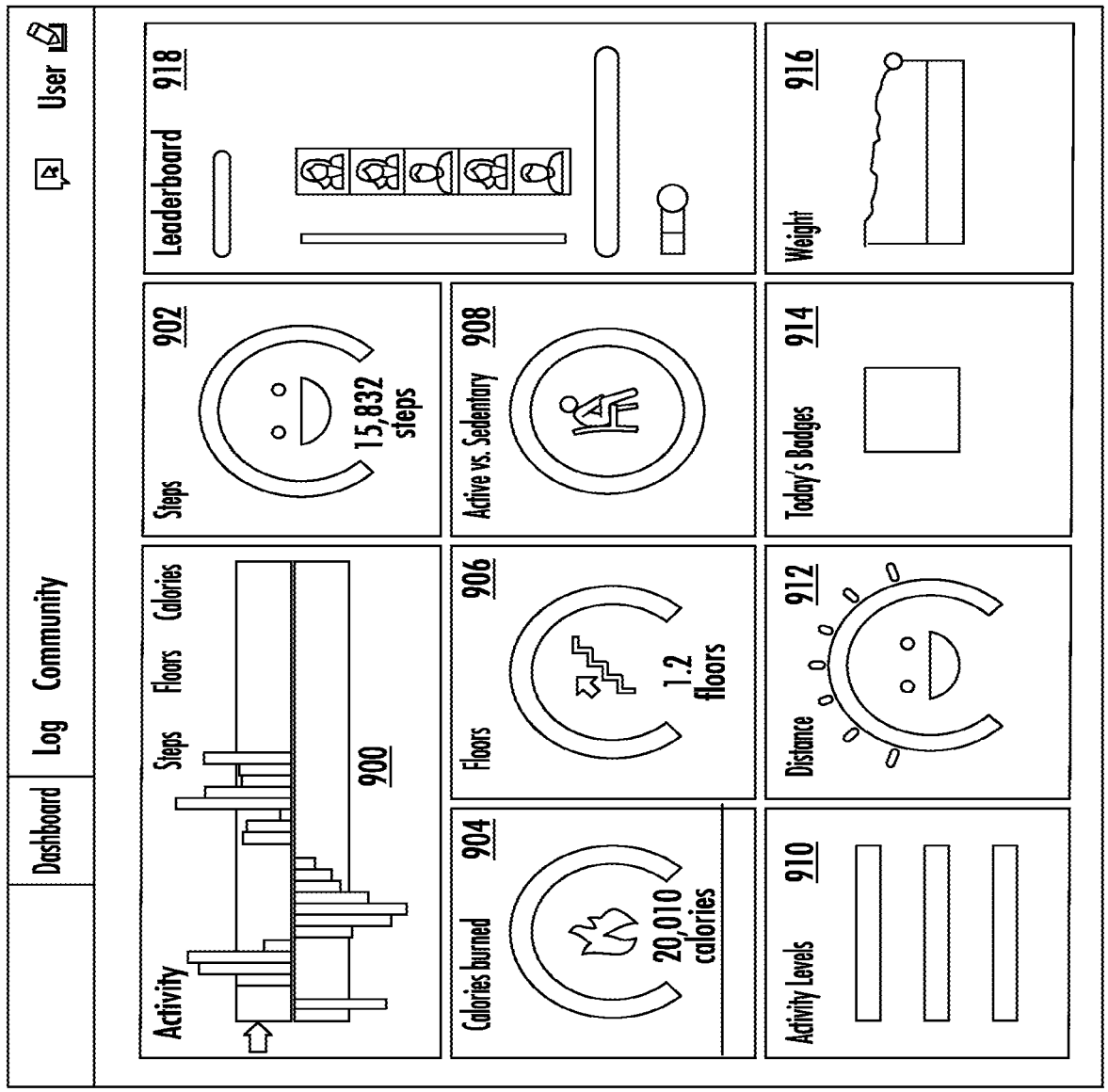
FIG. 9 illustrates a graphical user interface for accessing activity related information of a user based on an activity monitoring device, in accordance with an embodiment of the invention.

FIG. 9 illustrates a graphical user interface for accessing activity related information of a user based on an activity monitoring device, in accordance with an embodiment of the invention. In the illustrated embodiment, a number of informational panels or modules are shown, providing information about various aspects of the user's activity as defined based on data from an activity monitoring device. An activity module 900 is configured to provide a graphical display of the number of steps taken, floors climbed, or calories burned over time. A steps module 902 is configured to display a number of steps taken by a user over a given time period. A calories burned module 904 is configured to display a number of calories burned over a given time period. A floors module 906 is configured to display a number of floors climbed by the user over a given time period. An active versus sedentary module 908 is configured to display relative amounts of time spent by the user in active physical activity versus sedentary activity. An activity levels module 910 is configured to display amount of time spent at various activity levels. A distance module 912 is configured to display a distance traveled by the user over a given period of time. A badges module 914 is configured to display badges or other types of milestone related data based on the activity of the user. A weight module 916 is configured to display current and/or historical weight data to the user.

A friends module 918 is configured to display friends of the user that may be in a social graph associated with the user. In one embodiment, the friends module 918 can be configured to provide a leaderboard display wherein activity data/metrics associated with friends of the user are shown, and wherein such friends may be listed in a ranked order based on the activity data/metrics, thereby providing a leaderboard with respect to a given activity data or metric. It will be appreciated that the user may select a given friend identified by the friends module 918 and generate or define a notification to be sent to the selected friend. Additionally, it is noted that notifications may be generated based on activity data/metrics associated with friends of the user, such as informational notifications when a friend achieves a certain goal or milestone, when a friend surpasses the user with respect to particular activity data/metrics, when the user surpasses a friend with respect to particular activity data/metrics, etc.

Figure 10A:
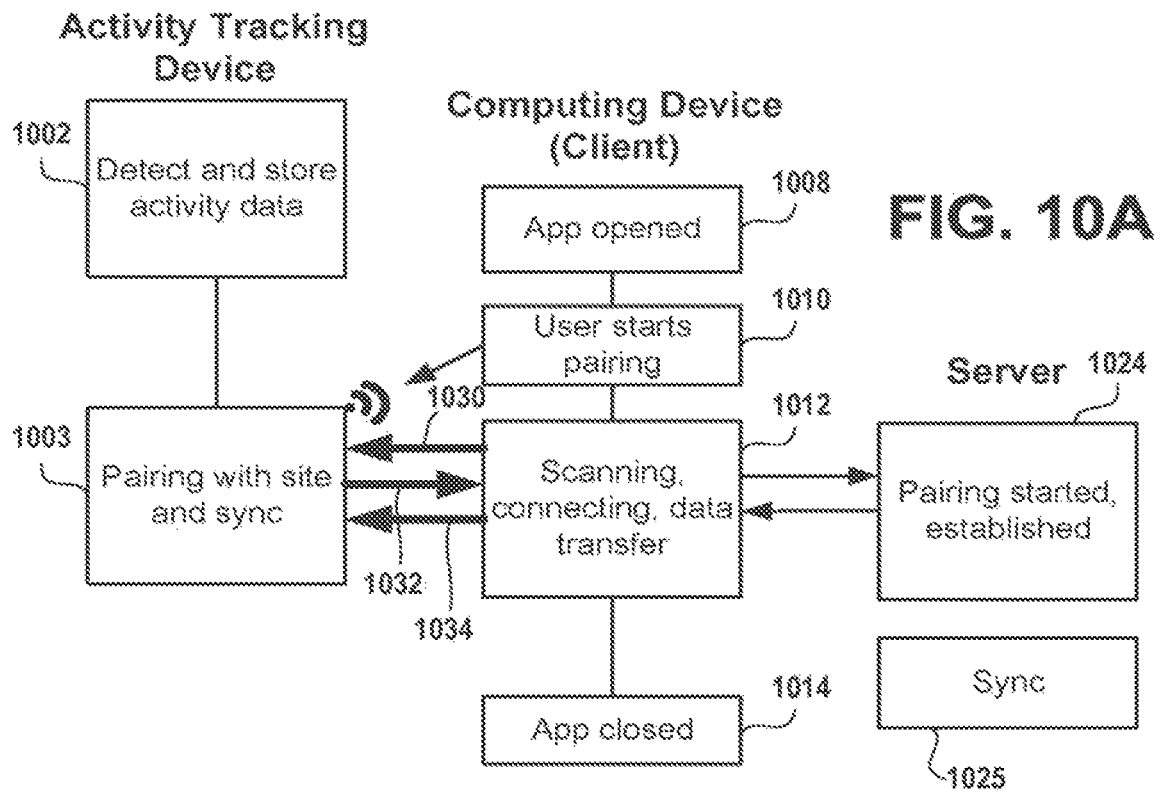
FIGS. 10A-10C illustrate embodiments of communication operations between an activity tracking device, a client device, and a backend server, in accordance with one embodiment of the present invention.
Figure 10B:
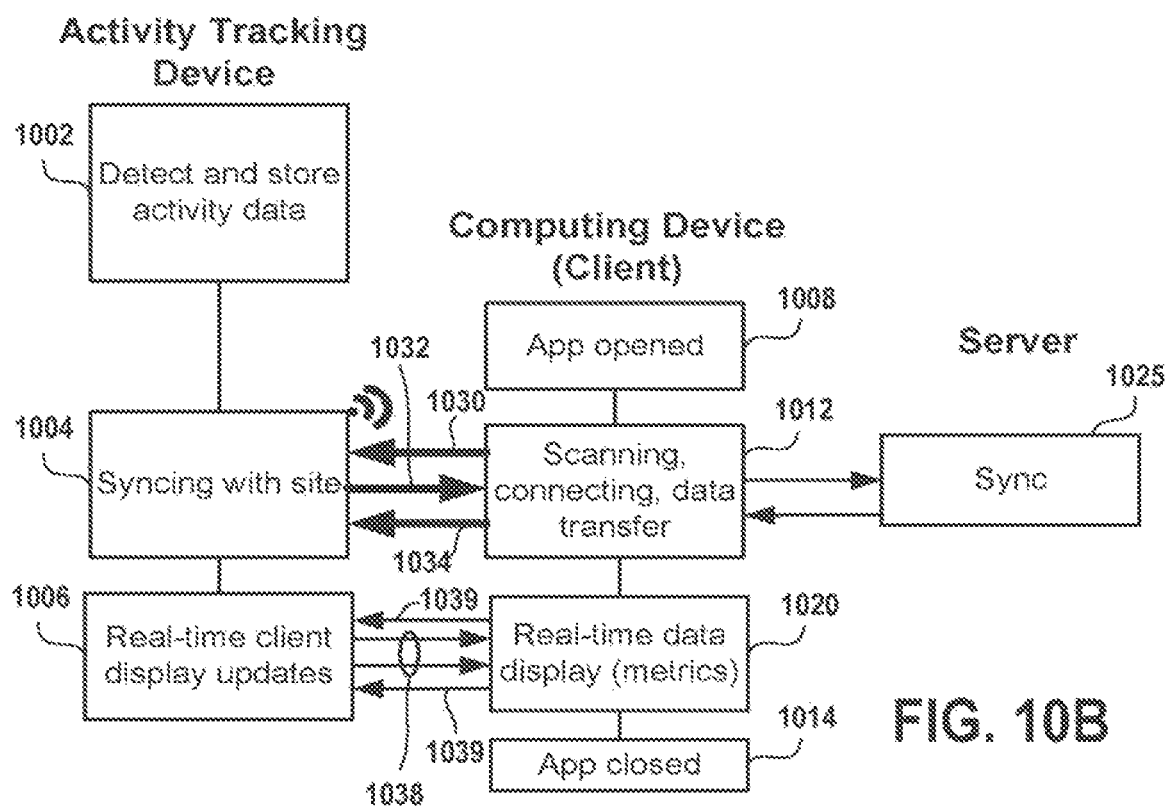
Figure 10C:
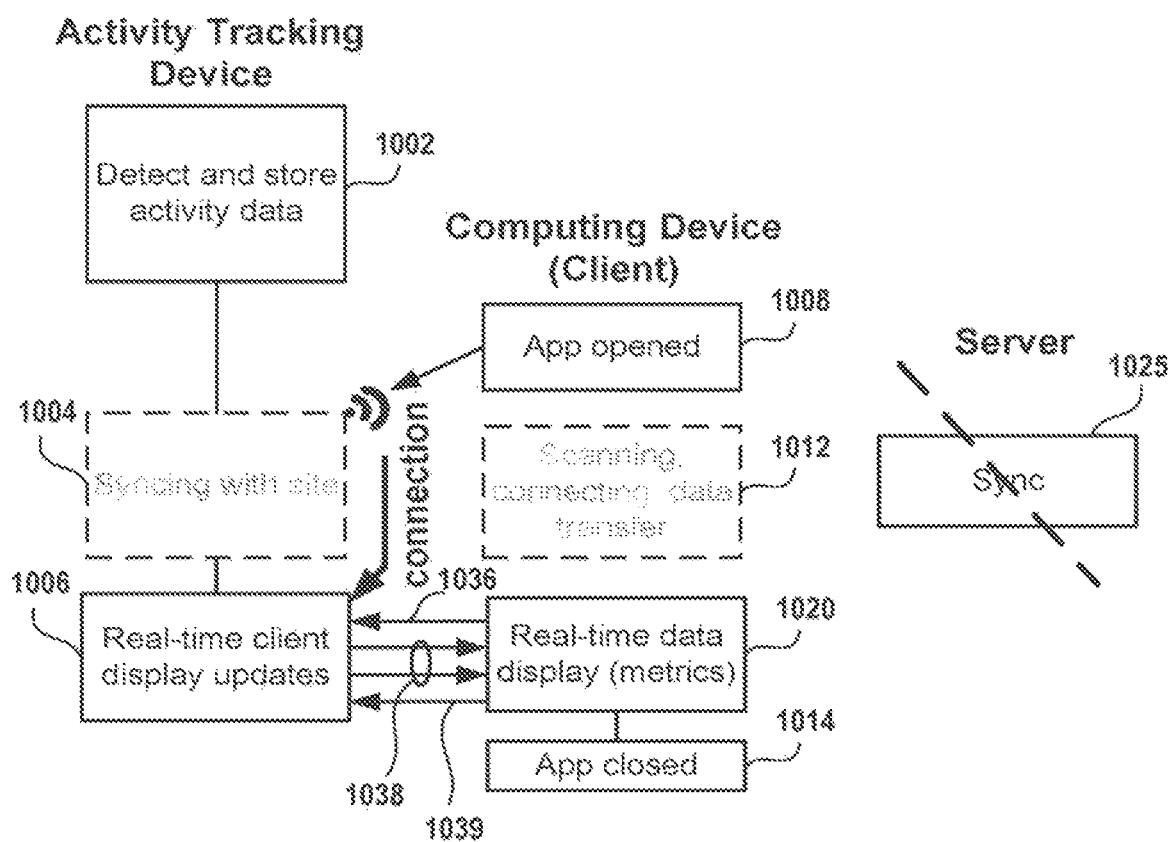

FIGS. 10A-10C illustrate embodiments of communication operations between an activity tracking device, a client device, and a backend server, in accordance with one embodiment of the present invention.

The communication described with reference to the flow diagrams in FIGS. 10A-10C should only be viewed as exemplary of operations that occur between the activity tracking device, a client device (computing device), and a backend server (server). In this illustrated example, thick pointed arrows indicate that a connection interval has been scaled up so as to operate data transfers at a first data transfer rate, while a thin pointed arrow indicates a connection interval that has been scaled down so as to operate data transfers at a second data transfer rate.

In one embodiment, the first transfer rate is designed to allow the transfer of larger amounts of data that have been stored on the activity tracking device over a period of time, such as since the last connection was made to a computing device. The activity tracking data stored on the activity tracking device can include, for example, motion data associated with the various activities performed by a user, data sensed by the activity tracking device, or data measured by the activity tracking device.

The various activities may include, without limitation, walking, running, jogging, walking up and down stairs, and general movement. Other information that can be stored by the activity tracking device can include, for example, measured information such as heart rate information, temperature information, etc. In one embodiment, storage of the activity tracking device will store this information for a period of time until a connection is made to a client device, such as a computing device configured to sync with the activity tracking device. In one embodiment, the computing device (client device) can be a smart phone, a tablet computer, a laptop computer, a desktop computer, or a general computing device.

In one embodiment, the first transfer rate is defined by scaling up the connection interval of the communication channel established between the activity tracking device and the client device. For example, if the communication channel is a low energy Bluetooth connection, the connection interval can be scaled to enable a transfer of packets that is more frequent than the second transfer rate.

First Transfer Rate (Connection Interval Scale-Up)

The connection interval for the first transfer rate can be scaled up to set a throughput of packets, such that each packet is transferred in less than about 200 milliseconds (ms). In one example embodiment, the first transfer rate is set to transfer one packet every about 10 ms to about 30 ms. In another example embodiment, the first transfer rate can be one packet every about 20 ms. In one embodiment, each packet is about 20 bytes.

In one embodiment, the first data transfer rate may be defined in terms of a frequency, in a range of between about 500 Bps (bytes per second) and about 2 kBps (kilobytes per second). In one example data transfer rate is about 1 kBps (kilobyte per second).

Second Transfer Rate (Connection Interval Scale-Down)

The connection interval for the second transfer rate can scaled down to set a throughput of packets, such that each packet is transferred at an interval that is greater than about 200 milliseconds (ms). In one example embodiment, the second transfer rate is set to transfer a packet every 500 ms. In some embodiments, depending on the frequency of events or lack of events, the transfer rate can be set to update only after several seconds (e.g., about 1-10 seconds). In one embodiment, each packet is about 20 bytes.

In one embodiment, the second data transfer rate may define a frequency value that is less than 500 bps (bytes per second). In another embodiment, the second data transfer rate can be set to a value that is less than 100 bps (bytes per second). In still another example, the second data transfer rate can be about 1 Bps (1 byte per second). In some embodiments, depending on the frequency of events or lack of events, the transfer rate can be scaled down even further.

It should be understood that these example rates, parameters, and/or sizes can change over time, depending on standards, customizations, and/or optimizations. So therefore, these parameters should only be viewed as examples. It is further understood that the methods and devices defined herein can implement embodiments that include more than two data transfer rates. In fact, the number of data transfer rates can include any number, based on a number of pre-defined scaled up or scaled down connection intervals. The number of intervals will vary, of course, depending on the implementation.

By scaling the connection intervals up or down, it is not the actual throughput that is being changed, but rather the possible bandwidth that can be supported by the channel. In the first data transfer rate, the scaled setting uses almost all of the channel bandwidth. In the second data transfer rate, most of the available channel bandwidth goes unused. A consideration for both transfer rates is latency, so the system does not want to have to wait too long before a single event (e.g., essentially one bit of information) can go from one device to another.

Returning to FIG. 10A, activity begins in operation 1002 where the activity tracking device detects and stores activity data associated with motion or data collected by the device. In the example of FIG. 10A, it is assumed that the activity tracking device has never been synchronized a website (e.g., site) of a server. Therefore, a pairing of the activity tracking device to the site needs to occur, at least once.

The client device, in operation 1008 may detect that an application is opened on the client device. The application that is opened is the activity tracking application 202, for example. In operation 1010, the client device begins to pair with the activity tracking device. Pairing may occur, for example, upon request of a user that initiates the pairing.

The pairing, in this embodiment is a pairing between the activity tracking device and the site, which is enabled via the computing device client. For example, the scanning, connecting and data transfer at the computing device will enable the pairing with the site. If the activity tracking device has activity data, it will also be synchronized with the site, as shown in 1024 and 1025. The communication between the computing device and the activity tracking device is carried out in accordance with the first transfer rate, which uses a scaled-up connection interval to transfer data. The first transfer rate can include, for example, command data 1030 requesting data from the activity tracking device, sending data 1032, and acknowledgement information 1034 for received data. At this point, the user may wish to close application 1014 at the client computing device.

In FIG. 10B, an example is shown of a connection where the activity tracking device had previously been paired to the site on the server, in accordance with one embodiment of the present invention. In operation 1002, activity data is detected and stored on the activity tracking device. At some point, an application is opened 1008 at the computing device. As noted above, the application may be an activity tracking application 202. An update condition is detected by the client device, which is identified by opening the application. The update condition will act to scale-up the connection interval, so as to set a first data transfer rate.

The thick arrows 1030, 1032 and 1034 represent the first data transfer rate, which is a faster transfer rate than the second transfer rate. Once the syncing with the site 1004 and sync 1025 is complete, using the scanning, connecting and data transfer 1012 of the client, the operation of real-time client display updates 1006 is processed.

The update condition has now changed, which causes a scale down of the connection intervals between the activity tracking device and the computing device. This, as noted above, causes the second transfer rate to govern for data exchanged to the computing device for real-time data display. In one embodiment, arrow 1036 indicates a request from the computing device for real time updates. Arrows 1038 indicate data transfers of any data available for transfer, using the second data transfer rate. Arrow 1039 indicate a command that the client device has closed the application 1014, so that the device can stop sending updates.

FIG. 10C illustrates an embodiment where the activity tracking device is connected to the computing device, without a connection with the server. Without server connection, the computing device (client) will not establish a pairing with the server, but instead will only establish a connection with the activity tracking device to perform real-time client display updates. As noted above, the activity tracking device will be set to communicate with the computing device using the second transfer rate, which is a result of scaling down the connection interval for performing the transfer of updates.

In this embodiment, the transfer of updates takes place to the computing device, which can display updates from the tracker in substantial real time. In one embodiment, the updates are transferred at a rate that is substantially not noticeable to a user viewing a changing screen or display of the computing device (e.g., the display of a smartphone, a smart watch, glasses device, etc.). In one example, the substantial real-time updates occur with transfer delay to the display that is less than about 2 seconds. In other embodiments, the transfer delay is less than about 1 second. In still other embodiments, the transfer delay is less than about 0.6 second. To human perception, the updates would appear to occur in real-time, wherein the updated activity data is continuously updated to the client device, and the display changes continuously or intermittently, depending on whether activity was captured or not. In some embodiments, the real time display will show numbers on a screen changing, such as counting steps, counting stairs, showing distance traveled, etc.

The communication between the client device and the server is executed using an Internet connection link, such as a Wi-Fi connection or cellular connection. As noted in this disclosure, the activity tracking device can be a wearable device on the wrist of a user, or a device that can be held by the user or attached to the user's clothing. As the user engages in motion or activities, the captured information can be transferred directly to the client device, such as a smart phone having an activity tracking application.

If the activity tracking application is open, and the user is viewing one or more screens or data provided by the activity tracking application, that motion or activity data is transferred to the smart phone for display. Thus, if the user is currently viewing a screen that displays metric data associated with the activity being performed by the user, that activity can be updated substantially in real time as the user engages in the activity. For example, if the user is walking while viewing the screen that displays the number of steps, the number of steps can be shown to increase as the user is walking and viewing the display on the smart phone.

As the flow diagrams of FIGS. 10A-10C show, communication is managed between activity tracking device, the computing device, and the backend server. However, it should be understood that the communication between the activity tracking device and the client device can occur without having any Internet connection or connections to the backend server, as noted with response to FIG. 10C. When Internet connection is established by the client device at some point, the client device can then synchronize with the backend server, such as during background syncs, or when the app on the client device is again opened.

Figure 11:
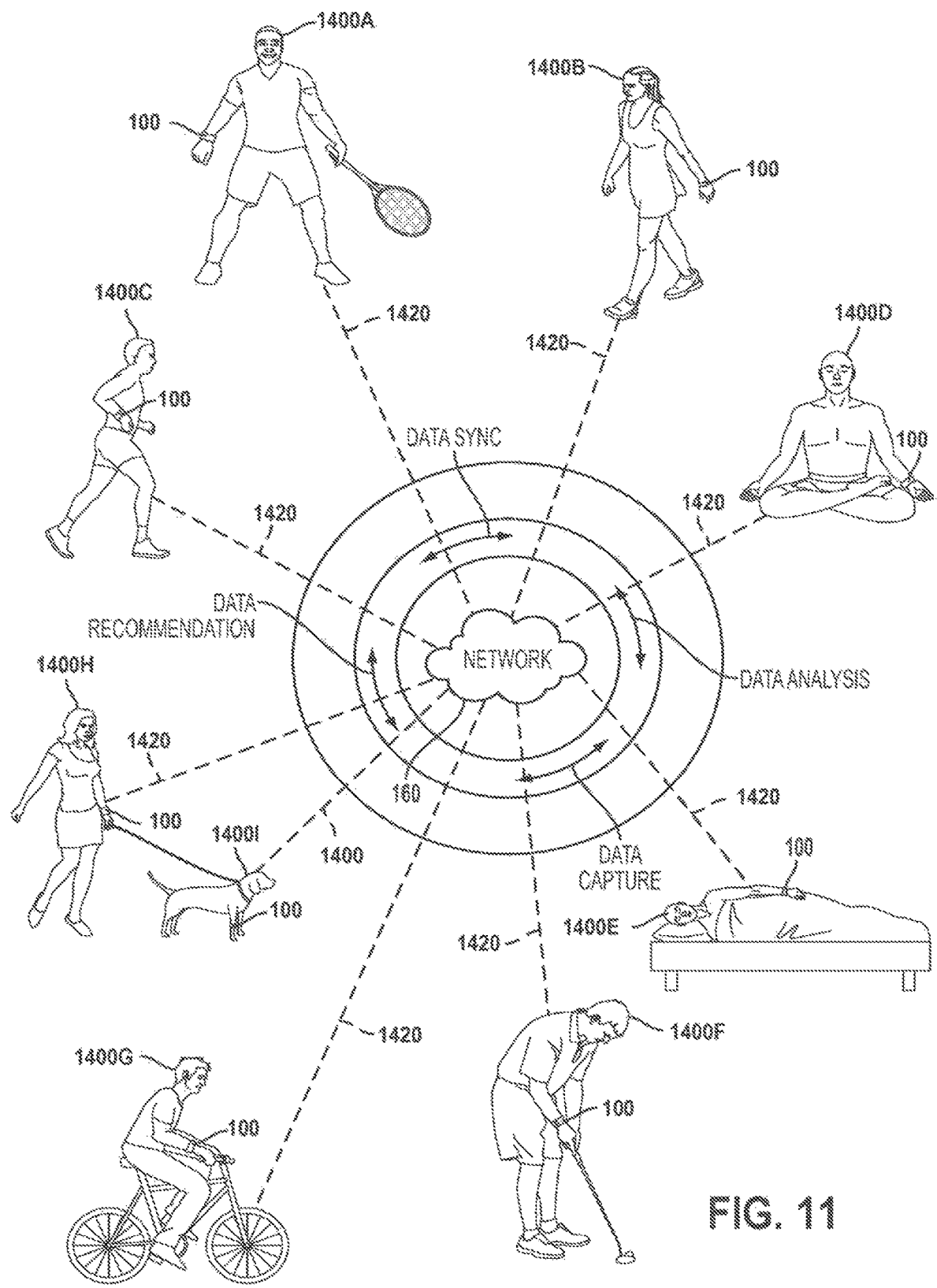
FIG. 11 illustrates an example where various types of activities of users can be captured or collected by activity tracking devices, in accordance with various embodiments of the present invention.

FIG. 11 illustrates an example where various types of activities of users 1400A-1400I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 1420 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming stroke/lap count, racquet swings/hits, golf swings, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration (e.g. number of time awoken), pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. An apparatus, comprising:
   a processor;
   a memory;
   a display; and
   a wireless module,
   wherein the memory, the processor, the display, and the wireless module are operatively connected, and wherein the memory stores computer-executable instructions for controlling the processor to:
      receive, from a wearable device and via the wireless module, activity data indicative of an activity metric of a user on a periodic basis,
      determine the activity metric based on the activity data,
      determine progress towards a first activity goal based on the activity metric, and
      provide a notification at one or more predetermined times, wherein the notification indicates progress towards the first activity goal.

2. The apparatus of claim 1, wherein the one or more predetermined times for providing the notification is daily.

3. The apparatus of claim 1, wherein the memory stores further computer-executable instructions for furthering controlling the processor to:
   determine a predetermined window of time during which to provide the notification, and
   schedule at least one of the one or more predetermined times for providing the notification to be within the predetermined window of time.

4. The apparatus of claim 1, wherein the memory stores further computer-executable instructions for furthering controlling the processor to:
   determine that the user is busy or occupied at the one or more predetermined times; and
   delay providing the notification at the one or more predetermined times that it is determined that the user is busy or occupied.

5. The apparatus of claim 4, wherein the memory stores further computer-executable instructions for furthering controlling the processor to determine that the user is busy or occupied based on the activity data from the wearable device.

6. The apparatus of claim 4, wherein the memory stores further computer-executable instructions for furthering controlling the processor to determine that the user is busy or occupied based on a calendar associated with the user.

7. The apparatus of claim 4, wherein the memory stores further computer-executable instructions for furthering controlling the processor to determine that the user is busy or occupied based on a location of the user.

8. The apparatus of claim 1, wherein the memory stores further computer-executable instructions for furthering controlling the processor to:
   determine a rate of change of the activity metric;
   determine the rate of change of the activity metric exceeds a threshold; and
   based on the rate of change of the activity metric exceeding the threshold, providing another notification.

9. The apparatus of claim 1, wherein the memory stores further computer-executable instructions for furthering controlling the processor to:
   determine that a current amount of the activity metric during a current interval of time is higher than the highest amount of the activity metric during each of one or more prior intervals of time; and
   generate the notification based on the current amount of the activity metric during a current interval of time being higher than the highest amount of the activity metric during each of the one or more prior intervals of time.

10. The apparatus of claim 1, wherein the memory stores further computer-executable instructions for furthering controlling the processor to:
    establish a plurality of thresholds associated with the first activity goal, each threshold of the plurality of thresholds associated with a different value of the activity metric, and
    provide a separate notification responsive to each time one of the thresholds is met or exceeded by the activity metric.

11. A method, comprising:
    receiving, from a wearable device, activity data indicative of an activity metric of a user on a periodic basis,
    determining the activity metric based on the activity data,
    determining progress towards a first activity goal based on the activity metric, and
    providing a notification at one or more predetermined times, wherein the notification indicates progress towards the first activity goal.

12. The method of claim 11, wherein the one or more predetermined times for providing the notification is daily.

13. The method of claim 11, further comprising:
determining a predetermined window of time during which to provide the notification, and
scheduling at least one of the one or more predetermined times for providing the notification to be within the predetermined window of time.

14. The method of claim 11, further comprising:
determining a rate of change of the activity metric;
determining the rate of change of the activity metric exceeds a threshold; and
based on the rate of change of the activity metric exceeding the threshold, causing a second notification to be provided.

15. The method of claim 11, further comprising:
determining that a current amount of the activity metric during a current interval of time is higher than the highest amount of the activity metric during each of one or more prior intervals of time; and
generating the notification based on the current amount of the activity metric during a current interval of time being higher than the highest amount of the activity metric during each of the one or more prior intervals of time.

16. A non-transitory machine-readable storage medium that includes computer-executable instructions which, when executed by one or more processors, cause the one or more processors to:
receive, from a wearable device, activity data indicative of an activity metric of a user on a periodic basis,
determine the activity metric based on the activity data,
determine progress towards a first activity goal based on the activity metric, and
providing a notification at one or more predetermined times, wherein the notification indicates progress towards the first activity goal.

17. The non-transitory machine-readable storage medium of claim 16, wherein the one or more predetermined times for providing the notification is daily.

18. The non-transitory machine-readable storage medium of claim 16, storing further computer-executable instructions for controlling the one or more processors to:
determine a predetermined window of time during which to provide the notification, and
schedule at least one of the one or more predetermined times for providing the notification to be within the predetermined window of time.

19. The non-transitory machine-readable storage medium of claim 16, storing further computer-executable instructions for controlling the one or more processors to:
determine a rate of change of the activity metric;
determine the rate of change of the activity metric exceeds a threshold; and
based on the rate of change of the activity metric exceeding the threshold, providing another notification.

20. The non-transitory machine-readable storage medium of claim 16, storing further computer-executable instructions for controlling the one or more processors to:
determine that a current amount of the activity metric during a current interval of time is higher than the highest amount of the activity metric during each of one or more prior intervals of time; and
generate the notification based on the current amount of the activity metric during a current interval of time being higher than the highest amount of the activity metric during each of the one or more prior intervals of time.

* * * * *